United States Patent
Bentley et al.

(12)

(10) Patent No.: US 6,706,750 B1
(45) Date of Patent: Mar. 16, 2004

(54) INDOLE DERIVATIVES PROCESS FOR THEIR PREPARATION, PHARMACEUTICAL COMPOSITIONS CONTAINING THEM AND THEIR MEDICINAL APPLICATION

(75) Inventors: Jonathan Mark Bentley, Wokingham (GB); Jonathan Richard Anthony Roffey, Wokingham (GB); James Edward Paul Davidson, Wokingham (GB); Howard Langham Mansell, Wokingham (GB); Richard John Hamlyn, Wokingham (GB); Ian Anthony Cliffe, Wokingham (GB); David Reginald Adams, Wokingham (GB); Nathaniel Julius Monck, Wokingham (GB)

(73) Assignee: Vernalis Research Limited, Wokingham (GB)

( * ) Notice: Subject to any disclaimer, the term of this patent is extended or adjusted under 35 U.S.C. 154(b) by 65 days.

(21) Appl. No.: 10/009,568

(22) PCT Filed: Aug. 4, 2000

(86) PCT No.: PCT/GB00/03011

§ 371 (c)(1),
(2), (4) Date: Mar. 11, 2002

(87) PCT Pub. No.: WO01/12603

PCT Pub. Date: Feb. 22, 2001

(30) Foreign Application Priority Data

Aug. 11, 1999 (GB) .............................. 9918962

(51) Int. Cl.$^7$ .................. A61K 31/40; A61P 43/00; C07D 491/02
(52) U.S. Cl. .................. 514/411; 548/431; 548/449
(58) Field of Search .................... 514/411; 548/431, 548/449

(56) References Cited

U.S. PATENT DOCUMENTS

| 2,541,211 A | | 2/1951 | Cusic et al. |
| 2,687,414 A | | 8/1954 | Cusic |
| 3,142,678 A | * | 7/1964 | Rice et al. ............... 260/247.1 |
| 3,329,571 A | | 7/1967 | Rice et al. |

FOREIGN PATENT DOCUMENTS

| DE | 930 988 | 7/1955 |
| EP | 0 655 440 | 5/1995 |
| EP | 0 657 426 | 6/1995 |
| EP | 0 700 905 | 3/1996 |
| GB | 1013908 | 12/1965 |
| JP | 47-13661 | * 4/1976 |
| WO | WO 98 30548 | 7/1998 |

OTHER PUBLICATIONS

Nishiguchi, et al, Biological Psychiatry, 2001, 50, 123–128.*
Dean, B., J. Neurochem., 2003, 85, 1–13.*
Spiller, et al, J. Clin. Pharmacol., 2002, 54, 11–20.*

* cited by examiner

Primary Examiner—Joseph K. McKane
Assistant Examiner—Andrea D. Small
(74) Attorney, Agent, or Firm—Foley & Lardner

(57) ABSTRACT

A chemical compound of formula (I) wherein: $R_1$ and $R_2$ are independently selected from hydrogen and alkyl; $R_3$ is alkyl; $R_4$, $R_6$ and $R_7$ are independently selected from hydrogen, halogen, hydroxy, alkyl, aryl, amino, alkylamino, dialkylamino, alkoxy, aryloxy, alkylthio, alkylsufoxyl, alkylsulfonyl, nitro, carbonitrile, carbo-alkoxy, carbo-aryloxy and carboxyl; $R_5$ is selected from hydrogen, halogen, hydroxy, alkyl, aryl, amino, alkylamino, dialkylamino, alkoxy, aryloxy, alkylthio, alkylsulfoxyl, alkylsulfonyl, nitro, carbonitrile, carbo-alkoxy, carbo-aryloxy and carboxyl; A is a 5- or 6-membered partially unsaturated or aromatic heterocyclic ring or a 5- or 6-membered partially unsaturated carbocyclic ring, wherein if A is a 6-membered partially unsaturated carbocyclic ring then at least one of $R_4$ to $R^7$ is other than hydrogen, and pharmaceutically acceptable salts, addition compounds and prodrugs thereof, and the use thereof in therapy, particularly as an agonist or antagonist of a 5HT receptor, particularly a $5HT_{2C}$ receptor, for instance in the treatment of disorders of the central nervous system; damage to the central nervous system; cardiovascular disorders; gastrointestinial disorders; diabetes insipidus, and sleep apnea, and particularly for the treatment of obesity.

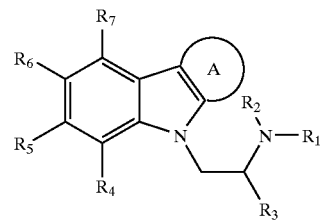

(I)

23 Claims, No Drawings

INDOLE DERIVATIVES PROCESS FOR THEIR PREPARATION, PHARMACEUTICAL COMPOSITIONS CONTAINING THEM AND THEIR MEDICINAL APPLICATION

This application is a 371 of PCT/GB00/03011 Aug. 4, 2000.

The present invention relates to indole derivatives, to processes and intermediates for their preparation, to pharmaceutical compositions containing them and to their medicinal use. The active compounds of the present invention are useful in treating obesity and other disorders.

It has been recognised that obesity is a disease process influenced by environmental factors in which the traditional weight loss methods of dieting and exercise need to be supplemented by therapeutic products (S. Parker, "*Obesity: Trends and Treatments*", Scrip Repons, PJB Publications Ltd, 1996).

Whether someone is classified as overweight or obese is generally determined on the basis of their body mass index (BMI) which is calculated by dividing body weight (kg) by height squared ($m^2$). Thus, the units of BMI are $kg/m^2$ and it is possible to calculate the BMI range associated with minimum mortality in each decade of life. Overweight is defined as a BMI in the range 25–30 $kg/m^2$, and obesity as a BMJ greater than 30 $kg/m^2$. There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (Reductil®) and Sibutramine. Orlistat (a lipase inhibitor) inhibits fat absorption directly and tends to produce a high incidence of unpleasant (though relatively harmless) side-effects such as diarrhoea Sibutramine (a mixed 5-HT/noradrenaline reuptake inhibitor) can increase blood pressure and heart rate in some patients. The serotonin releaser/reuptake inhibitors fenfluramine (Pondimin®) and dexfenflurarmine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

The non-selective $5\text{-HT}_{2C}$ receptor agonists/partial agonists m-chlorophenylpiperazine (mCPP) and trifluoromethylphenylpiperazine (TFWPP) have been shown to reduce food intake in rats (G. A. Kennett and G. Curzon, *Psychopharmacol.*, 1988, 98, 93–100; G. A. Kennett, C. T. Dourish and G. Curzon, *Eur. J. Pharmacol.*, 1987, 141, 429453) and to accelerate the appearance of the behavioural satiety sequence (S J. Kitchener and C. T. Dourish, *Psychopharmacol.*, 1994, 113, 369–377). Recent findings from studies with mCPP in normal human volunteers and obese subjects have also shown decreases in food intake. Thus, a single injection of mCPP decreased food intake in female volunteers (A. E. S. Walsh et al., *Psychopharmacol.*, 1994, 116, 120–122) and decreased the appetite and body weight of obese male and female subjects during subchronic treatment for a 14 day period (P. A. Sargeant et al., *Psychopharmacol.*, 1997, 113, 309–312). The anorectic action of mCPP is absent in $5\text{-HT}_{2C}$ receptor knockout mutant mice (L. H. Tecott et al., *Nature*, 1995, 374, 542–546) and is antagonised by the $5\text{-HT}_{2C}$ receptor antagonist SB-242084 in rats (G. A. Kennett et al., *Neuropharmacol.*, 1997, 36, 609–620). It seems therefore that mCPP decreases food intake via an agonist action at the $5\text{-HT}_{2C}$ receptor.

Other compounds which have been proposed as $5\text{-HT}_{2C}$ receptor agonists for use in the treatment of obesity include the substituted 1-aminoethyl indoles disclosed in EP-A-0655440. CA-2132887 and CA-2153937 disclose that tricyclic 1-aminoethylpyrrole derivatives and tricyclic 1-aminoethyl pyrazole derivatives bind to $5\text{-HT}_{2C}$ receptors and may be used in the treatment of obesity. WO-A-98/30548 discloses aminoalkylindazole compounds as $5\text{-HT}_{2C}$ agonists for the treatment of CNS diseases and appetite regulation disorders. Substituted 1,2,3,4Tetrahydrocarbazoles have been reported as synthetic trypanocides in *J. Med. Chem.*, 1970, 13, 327 and *J. Med. Chem.*, 1973, 16, 1411. 9-(2-Dialkylaminopropyl)-1,2,3,4-tetrahydrocarbazoles have been disclosed in U.S. Pat. No. 2,687,414 and U.S. Pat. No. 2,541,211. 7-Substituted-9-(2-dialkylaminoethyl)-1,2,3,4-tetrahydrocarbazoles have been disclosed in DE 930988. The pharmacological behaviour of 2,3-polymethyleneindoles has been described in *J. Med. Chem.*, 1964, 69, 2910. Derivatives of polynuclear indoles have been described as antidepressants in *J. Med. Chem.*, 1964, 7, 625. Amino-substituted penthienoindoles with pharmacological properties are disclosed in U.S. Pat. No. 3,142,678. 1,2,3,4-Tetrahydro-cyclopent[b]indoles are disclosed in FR 2242983 and DE 2438413. 4(3-Aminobutyl)-1,2,3,4-tetrahydrocyclopent[b]indole has been described in *Khim. Geterotskikl. Soedin*, 1970, 6,371.

It is an object of this invention to provide selective, directly acting $5HT_2$ receptor ligands for use in therapy and particularly for use as anti-obesity agents. It is a further object of this invention to provide directly acting ligands selective for $5\text{-HT}_{2B}$ and/or $5\text{-HT}_{2C}$ receptors, for use in therapy and particularly for use as anti-obesity agents. It is a further object of this invention to provide selective, directly acting $5\text{-HT}_{2C}$ receptor ligands, preferably $5\text{-HT}_{2C}$ receptor agonists, for use in therapy and particularly for use as anti-obesity agents.

According to the present invention there is provided a chemical compound of formula (I):

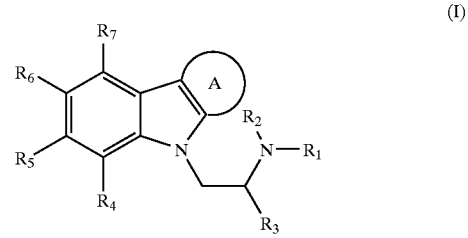

wherein:
  $R_1$ and $R_2$ are independently selected from hydrogen and alkyl;
  $R_3$ is alkyl;
  $R_4$, $R_6$ and $R_7$ are independently selected from hydrogen, halogen, hydroxy, alkyl, aryl, amino, alkylamino, dialkylamino, alkoxy, aryloxy, alkylthio, alkylsulfoxyl, alkylsulfonyl, nitro, carbonitrile, carbo-alkoxy, carbo-aryloxy and carboxyl;

$R_5$ is selected from hydrogen, halogen, hydroxy, alkyl, aryl, amino, alkylamino, dialkylamino, alkoxy, aryloxy, alkylthio, alkylsulfoxyl, alkylsulfonyl, nitro, carbonitrile, carbo-alkoxy, carbo-aryloxy and carboxyl; and A is a 5- or 6-membered partially unsaturated or aromatic heterocyclic ring or a 5- or 6-membered partially unsaturated carbocyclic ring, wherein if A is a 6-membered partially unsaturated carbocyclic ring then at least one of $R_4$ to $R_7$ is other than hydrogen, and pharmaceutically acceptable salts, addition compounds and prodrugs thereof.

As used herein, the term "alkyl" means a branched or unbranched, cyclic or acyclic, saturated or unsaturated (e.g. alkenyl or alkynyl) hydrocarbyl radical. Where cyclic, the alkyl group is preferably $C_3$ to $C_{12}$, more preferably C5 to $C_{10}$. Where acyclic, the alkyl group is preferably $C_1$ to $C_{10}$, more preferably $C_1$ to $C_6$, more preferably methyl ethyl, propyl (n-propyl or isopropyl), butyl (n-butyl, isobutyl or tertiary-butyl) or pentyl (including n-pentyl and iso-pentyl), more preferably methyl. It will be appreciated therefore that the term "alkyl" as used herein includes alkyl (branched or unbranched), alkenyl (branched or unbranched), alkynyl (branched or unbranched), cycloalkyl cycloalkenyl and cycloalkynyl.

As used herein, the term "lower alkyl" means a branched or unbranched, cyclic or acyclic, saturated or unsaturated (e.g alkenyl or alkynyl) hydrocarbyl radical, wherein a cyclic lower alkyl group is $C_5$, $C_6$ or $C_7$, and wherein an acyclic lower alkyl group is methyl, ethyl, propyl (n-propyl or isopropyl) or butyl (n-butyl, isobutyl or tertiary-butyl), more preferably methyl.

As used herein, the term "aryl" means an aromatic group, such as phenyl or naphthyl, or a heteroaromatic group containing one or more heteroatom, such as pyridyl, pyrrolyl quinolinyl furanyl, thienyl, oxadiazolyl, thiadiazolyl, thiazolyl, oxazolyl isoxazolyl pyrazolyl, triazolyl, imidazolyl or pyrimidinyl.

As used herein, the term "alkoxy" means alkyl-O—. As used herein, the term "lower alkoxy" means loweralkyl-O—. As used herein, the term "aryloxy" means aryl-O—.

As used herein, the term "halogen" means a fluorine, chlorine, bromine or iodine radical, preferably a fluorine or chlorine radical.

As used herein the term "prodrug" means any pharmaceutically acceptable prodrug of the compound of formula (I) which is metabolised in vivo to a compound of formula (I).

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include acetic, benzenesulfonic, benzoic, camphorsulfonic, citric, dichloroacetic, ethanesulfonic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids, particularly fumaric acid. Acceptable base salts include alkali metal (e.g sodium, potassium), alkaline earth metal (e.g. calcium, magnesium) and aluminium salts.

As used herein, the term "addition compound" means any pharmaceutically acceptable addition compound of the compound of formula (I). Addition compounds include those which are formed without change of valency from the union between a compound of formula (I) and one or more other molecules, particularly solvates, hydrates and inclusion complexes (such as cyclodextrin complexes).

As used herein, the term "A is a 5- or 6-membered ring" refers to a ring containing 5 or 6 ring atoms in total, i.e. including the carbon atoms in the unsaturated positions of the indole ring to which A is fused.

As used herein, the term "carbocyclic ring" refers to a ring wherein all the ring atoms are carbon atoms.

As used herein, the term "partially unsaturated ring" refers to a ring which contains unsaturated ring atoms and one or more double bonds but which is not aromatic, for example a cyclohexenyl, cyclopentenyl, or thiacyclohexenyl ring. It will be appreciated therefore that a partially unsaturated ring A may contain one double bond, i.e. the double bond between the unsaturated 2 and 3 positions of the indole ring to which the ring A is fused, in which case the atoms of the ring A, other than the carbon atoms in the unsaturated 2 and 3 positions of the indole ring to which A is fused, are saturated. Alternatively, a partially unsaturated ring A may contain an additional double bond provided that this additional double bond does not result in the ring A being aromatic.

Where any of $R_1$ to $R_7$ is an alkyl group or an alkyl-containing group (such as alkoxy, alkylamino or alkylthio, for instance) as defined in formula (I) above, then that alkyl group, or the alkyl group of the alkyl-containing group, may be substituted or unsubstituted. Where any of $R_4$ to $R_7$ is an aryl group or an aryl-containing group (such as aryloxy, for instance) as defined in formula (I), then said aryl group, or the aryl group of the aryl-containing group, may be substituted or unsubstituted. The ring A may be substituted or unsubstituted, preferably unsubstituted. Where any of $R_1$ to $R_7$ or A is substituted, there will generally be 1 to 3 substituents present, preferably 1 substituent Substituents may include:

carbon-containing groups such as
    alkyl,
    aryl (e.g. substituted and unsubstituted phenyl),
    arylalkyl; (e.g. substituted and unsubstituted benzyl);
halogen atoms and halogen containing groups such as
    haloalkyl (e.g. trifluoromethyl),
    haloaryl (e.g. chlorophenyl);
oxygen containing groups such as
    oxo,
    alcohols (e.g. hydroxy, hydroxyalkyl, hydroxyaryl, (aryl)(hydroxy)alkyl),
    ethers (e.g. alkoxy, aryloxy, alkoxyalkyl, aryloxyalkyl, alkoxyaryl, aryloxyaryl),
    aldehydes (e.g. carboxaldehyde),
    ketones (e.g. alkylcarbonyl, arylcarbonyl, alkylcarbonylalkyl, alkylcarbonylaryl, arylcarbonylalkyl, arylcarbonylaryl, arylalkylcarbonyl, arylalkylcarbonylalkyl, arylalkylcarbonylaryl)
    acids (e.g. carboxy, carboxyalkyl, carboxyaryl),
    acid derivatives such as esters
        (e.g. alkoxycarbonyl, aryloxycarbonyl, alkoxycarbonylalkyl, aryloxycarbonylalkyl, alkoxycarbonylaryl, aryloxycarbonylaryl, alkylcarbonyloxy, alkylcarbonyloxyalkyl), amides (e.g. aminocarbonyl, mono- or di-alkylaminocarbonyl, aminocarbonylalkyl, mono- or di-alkylcarbonylalkyl, arylaminocarbonyl or arylalkylaminocarbonyl, alkylcarbonylamino, arylcarbonylamino or arylalkylcarbonyl amino), carbamates (eg. alkoxycarbonylamino, aryloxycarbonylamino, arylalkyloxycarbonylamino, aminocabonyloxy, mono- or di-alkylaminocarbonyloxy, arylaminocarbonyloxy or arylalkylaminocarbonyloxy) and ureas (eg. mono- or di-alkylaminocarbonylamino, arylaminocarbonylamino or aryalkylaminocarbonylamino);

nitrogen containing groups such as amines (e.g. amino, mono- or dialkylamino, arylamino, aminoalkyl, mono- or dialkylaminoalkyl), azides, nitriles (e.g. cyano, cyanoalkyl), nitro;

sulfur containing groups such as thiols, thioethers, sulfoxides, and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, alkylthioalkyl, arylsulfinylalkyl, arylsulfonylalkyl)

and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl 7-azaindolyl, benzopyranyl, coumarinyl, isocoumarinyl, quinolinyl, isoquinolinyl, naphthridinyl, cinnolinyl quinazolinyl, pyridopyridyl, benzoxazinyl, quinoxalinyl, chromenyl, chromanyl, isochromanyl, phthalazinyl, and carbolinyl).

It is preferred that the compounds of formula (I) are selected from those wherein $R_1$ to $R_7$ and A are as defined above with the proviso that if A is a 5- or 6-membered partially unsaturated carbocyclic ring then at least one of $R_4$ to $R_7$ is other than hydrogen.

In the compounds of formula (I), preferably $R_1$ and $R_2$ are independently selected from hydrogen and lower alkyl (preferably acyclic lower alkyl and more preferably methyl), and preferably from hydrogen.

In one embodiment, the compounds of formula (I) are selected from compounds in which $R_1$ is the same as $R_2$. Preferably, $R_1$ and $R_2$ are both hydrogen.

The compounds of formula (I) are preferably selected from compounds in which $R_3$ is lower alkyl, preferably acyclic lower alkyl, and more preferably methyl.

$R_5$ is selected from hydrogen, halogen, hydroxy, alkyl (including cycloalkyl, halo-alkyl (such as trifluoromethyl) and arylalkyl), aryl, amino, alkylamino, dialkylamino, alkoxy (including arylalkoxy), aryloxy, alkylthio, alkylsulfoxyl, alkylsulfonyl, nitro, carbonitrile, carbo-alkoxy, carbo-aryloxy and carboxyl.

In one embodiment, Rs is selected from halogen, hydroxy, alkyl (including cycloalkyl, halo-alkyl (such as trifluoromethyl) and arylalkyl), aryl, amino, alkylamino, dialkylamino, alkoxy (including arylalkoxy), aryloxy, alkylthio, alkylsulfoxyl, alkylsulfonyl, nitro, carbonitrile, carbo-alkoxy, carbo-aryloxy and carboxyl.

Preferably $R_5$ is selected from hydrogen, halogen and alkoxy, preferably from alkoxy and halogen, and preferably from alkoxy. Where $R_5$ is halogen, it is preferred that $R_5$ is selected from fluoro, chloro and bromo, preferably from fluoro and chloro and more preferably from fluoro. Where $R_5$ is selected from alkoxy, it is preferred that $R_5$ is selected from lower alkoxy, preferably acyclic lower alkoxy.

$R_4$, $R_6$ and $R_7$ are independently selected from hydrogen, halogen, hydroxy, alkyl (including cycloalkyl halo-alkyl (such as trifluoromethyl) and arylalkyl), aryl amino, alkylamino, dialkylamino, alkoxy (including arylalkoxy), aryloxy, alkylthio, alkylsulfoxyl, alkylsulfonyl, nitro, carbonitrile, carbo-alkoxy, carbo-aryloxy and carboxyl.

Preferably $R_4$ is selected from hydrogen, halogen, alkyl and alkoxy, and is preferably hydrogen Where $R_4$ is alkyl, it is preferred that $R_4$ is lower alkyl, preferably acyclic lower alkyl. Where $R_4$ is alkoxy, it is preferred that $R_4$ is lower alkoxy, preferably acyclic lower alkoxy.

Preferably $R_6$ is selected from hydrogen and halogen. Where $R_6$ is selected from halogen, $R_6$ is preferably fluoro or chloro, preferably fluoro.

Preferably $R_7$ is selected from hydrogen, halogen and alkoxy, preferably from hydrogen and halogen, and preferably from halogen. Where $R_7$ is alkoxy, it is preferred that $R_7$ is lower alkoxy, preferably acyclic lower alkoxy. Where $R_7$ is halogen, it is preferred that $R_7$ is selected from fluoro, chloro and bromo, preferably from chloro and bromo and preferably chloro.

It is preferred that at least one of $R_4$ to $R_7$ is a group other than hydrogen Where A is a heterocyclic ring, A may contain one or more heteroatom(s), and preferably only one heteroatom. Where A contains one or more heteroatom(s), it is preferred that the heteroatoms are selected from N, O and S. Where A is partially unsaturated, it is preferred that A contains no heteroatoms.

It is preferred that A is a 5-membered ring.

It is preferred that A is partially unsaturated, preferably wherein the atoms of the ring A, other than the carbon atoms in the unsaturated 2 and 3 positions of the indole ring to which the ring A is fused, are saturated.

In one embodiment, the compounds of formula (I) are selected from compounds wherein A is a 5-membered partially unsaturated carbocyclic ring, a 5-membered heterocyclic ring (preferably aromatic) or a 6membered partially unsaturated carbocyclic ring, preferably from compounds wherein A is a 5-membered partially u rated carbocyclic ring or a 5-membered heterocyclic ring, and more preferably from compounds wherein A is a 5-membered partially unsaturated carbocyclic ring.

In a further embodiment, the compounds of formula (I) are selected from compounds wherein A is selected from the group consisting of cyclopentenyl (including oxocyclopentenyl (particularly 1-oxocyclopent-4-enyl)), cyclohexenyl, thiacyclohexenyl (particularly 4-thiacyclohexenyl) and thienyl.

The compounds of the invention may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis. In a preferred embodiment of the invention, where all of $R_4$ to $R_7$ are hydrogen, the preferred stereochemistry at the carbon atom to which $R_3$ and $NR_1R_2$ are bound is (R). In an alternative embodiment, where $R_5$ or $R_7$ is a group other than hydrogen, the preferred stereochemistry at the carbon atom to which $R_3$ and $NR_1R_2$ are bound is (S).

In one embodiment of the invention, the compounds of formula (I) are preferably selected from:
(S)-1-(7,8-difluoro-1,2,3,4-tetrahydrocyclopent[b]indol-4-yl)-2-propylamine,
(S)-1-(7-fluoro-1,2,3,4-tetrahydrocyclopent[b]indol-4-yl)-2-propylamine,
(S)-1-(8-chloro-1,2,3,4-tetrahydrocyclopent[b]indol-4-yl)-2-propylamine,
(S)-1-(6-methoxy-1,2,3,4-tetrahydrocyclopent[b]indol-4-yl)-2-propylamine,
(S)-1-(7-fluoro-6-methoxy-1,2,3,4-tetrahydrocyclopent[b]indol-4-yl)-2-propylamine,
(S)-1-(7-fluoro-8-methoxy-1,2,3,4-tetrahydrocyclopent[b]indol-4yl)-2-propylamine,
(S)-1-(8-chloro-7-fluoro-1,2,3,4-tetrahydrocyclopent[b]indol-4-yl)-2-propylamine,
(S)-1-(1,2,3,4-tetrahydrocyclopent[b]indol-4-yl)-2-propylamine and
(R)-1-(1,2,3,4-tetrahydrocyclopent[b]indol-4-yl)-2-propylamine.

According to a further aspect of the invention, there is provided a compound of formula (I) for use in therapy.

The compounds of formula (I) may be used in the treatment (including prophylactic treatment) of disorders associated with 5-$HT_2$ receptor function. The compounds may act as receptor agonists or antagonists, preferably receptor agonists. Preferably, the compounds may be used in the treatment (including prophylactic treatment) of disorders associated with 5-$HT_{2B}$ and 5-$HT_{2C}$ receptor function. Preferably, the compounds may be used in the treatment (including prophylactic treatment) of disorders where 5-$HT_{2C}$ receptor activity is required, and preferably where a 5$HT_{2C}$ receptor agonist is required.

The compounds of formula (I) may be used in the treatment or prevention of central nervous disorders such as depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, personality disorders, age-related behavioural disorders, behavioural disorders associated with dementia, organic mental disorders, mental disorders in childhood, aggressivity, age-related memory disorders, chronic fatigue syndrome, drug and alcohol addiction, obesity, bulimia, anorexia nervosa or premenstrual tension; damage of the central nervous system such as by trauma stroke, neurodegenerative diseases or toxic or infective CNS diseases such as encephalitis or meningitis; cardiovascular disorders such as thrombosis; gastrointestinal disorders such as dysfunction of gastrointestinal motility; diabetes insipidus; and sleep apnea.

According to a further aspect of the invention, there is provided use of a compound of formula (I) in the manufacture of a medicament for the treatment (including prophylaxis) of the above-mentioned disorders. In a preferred embodiment, there is provided use of a compound of formula (I) in the manufacture of a medicament for the treatment (including prophylaxis) of obesity.

According to a further aspect of the invention, there is provided a method of treating a disorder selected from the group consisting of the above-mentioned disorders comprising administering to a patient in need of such treatment an effective dose of a compound of formula (I). In a preferred embodiment, there is provided a method of treatment (including prophylaxis) of obesity.

According to a further aspect of the invention, there is provided a pharmaceutical composition comprising a compound of formula (I) in combination with a pharmaceutically acceptable carrier or excipient and a method of making such a composition comprising combining a compound of formula (I) with a pharmaceutically acceptable carrier or excipient.

According to a further aspect of the invention, there is provided a method of preparing a compound of formula (I), for instance in the manner described below in the Reaction Schemes. $R_1$ to $R_7$ are as previously defined.

As used herein, the term "saturated 2,3-ring-fused indoles" refers to a tricyclic compound having a ring A as defined herein which is fused to an indole ring across the double bond in the 2- and 3-positions of the indole ring, wherein the atoms of the ring A, other than the carbon atoms in the unsaturated 2- and 3-positions of the indole ring to which A is fused, are saturated.

As used herein, the term "unsaturated 2,3-ring-fused indoles" refers to a tricyclic compound having a ring A as defined herein which is fused to an indole ring across the double bond in the 2- and 3-positions of the indole ring, wherein one or more of the atoms of the ring A, other than the carbon atoms in the unsaturated 2- and 3-positions of the indole ring to which A is fused, are unsaturated. It will be understood that the term "unsaturated 2,3-ring-fused indoles" includes compounds wherein the ring A is aromatic.

In Reaction Scheme 1, the saturated 2,3-ring-fused indoles (IV) may be formed by sequential reaction of the suitably substituted N-2-bromophenyl acetamide (eg $R=CF_3$) (II) with methyllithium and the appropriate 2-halocyclic ketone (III), followed by tert butyllithium and then trifluoroacetic acid. The N-alkyl ring-fused indole (V) (eg R=tert Bu) may then be obtained by reaction of (IV) with an appropriate carbamylethylsulfonate in the presence of a strong base such as potassium hydroxide in a solvent such as methyl sulfoxide. The indole (I) ($R_1=R_2=H$) may then be obtained by reaction of the indole (V) with a reagent suitable to reveal the protected amine function.

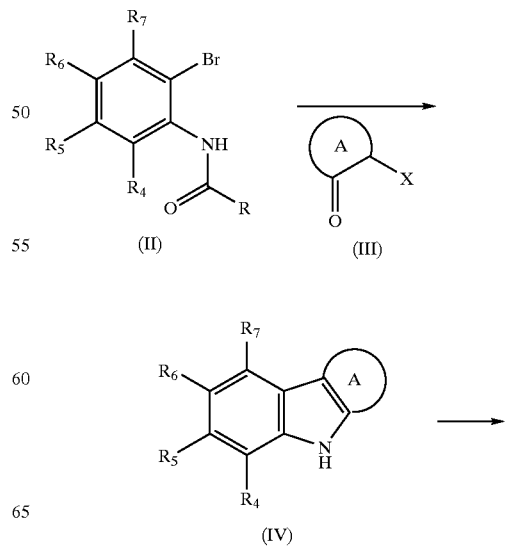

Reaction Scheme 1

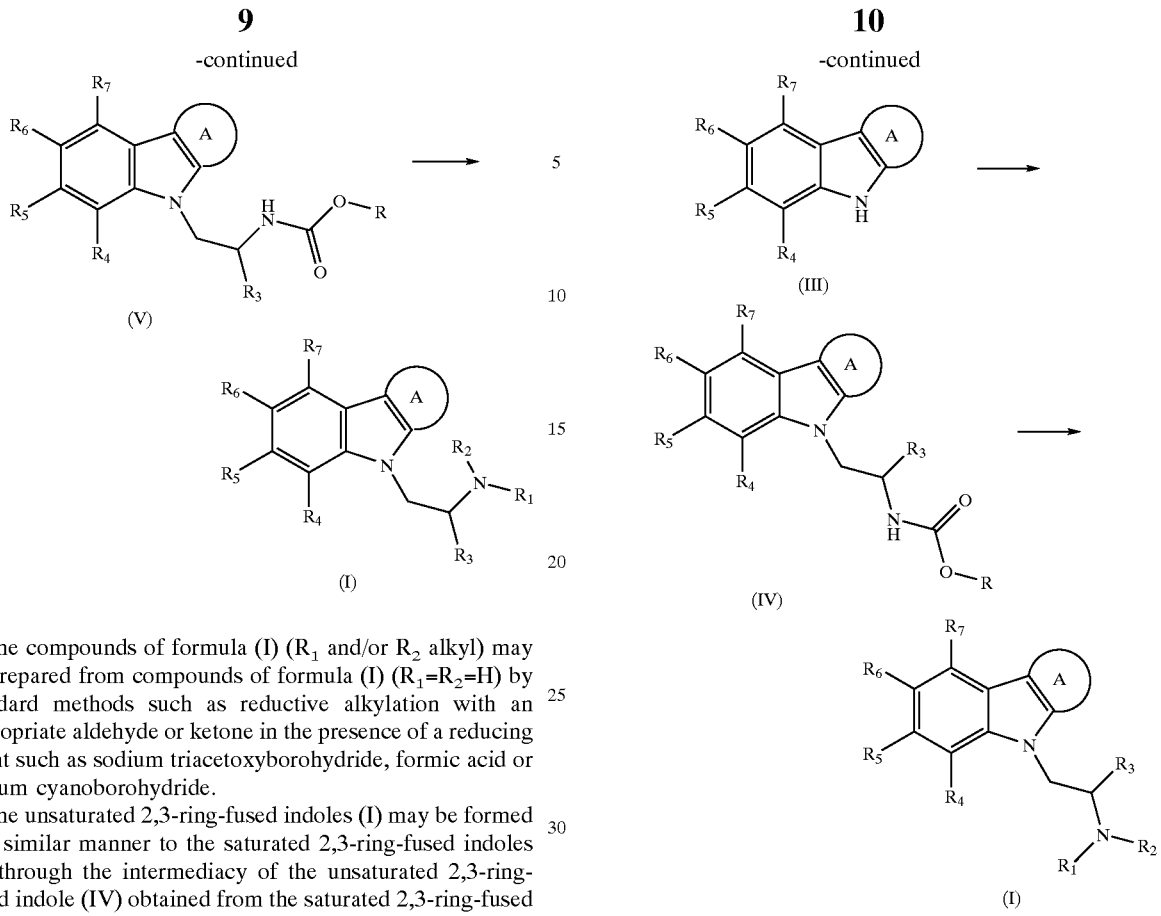

The compounds of formula (I) (R₁ and/or R₂ alkyl) may be prepared from compounds of formula (I) (R₁=R₂=H) by standard methods such as reductive alkylation with an appropriate aldehyde or ketone in the presence of a reducing agent such as sodium triacetoxyborohydride, formic acid or sodium cyanoborohydride.

The unsaturated 2,3-ring-fused indoles (I) may be formed in a similar manner to the saturated 2,3-ring-fused indoles (I), through the intermediacy of the unsaturated 2,3-ring-fused indole (IV) obtained from the saturated 2,3-ring-fused indole (IV) under standard dehyrogenation conditions such as through treatment with DDQ or Pd on carbon in a suitable solvent such as dioxan and xylene respectively.

Alternatively, compounds of the invention can be conveniently prepared according to Reaction Scheme 2. Treatment of phenylhydrazine (II) with a cyclic ketone under the acidic conditions in a suitable solvent, such as ethanol or water, produces indole (III). Reaction of indole (III) with an alkylating agent such as tert-butyl [2-[(1-methanesulfonyl)oxy]propyl]carbamate in the presence of a base such as potassium hydroxide in a suitable solvent e.g. methyl sulfoxide gives indolecarbamate (IV). A compound of formula (I) where R₁=R₂=H can be prepared by treatment of (IV) with an acid such as hydrochloric acid in a suitable solvent such as methanol or by use of a strong base such as potassium tert-butoxide in a solvent such as methyl sulfoxide. A compound of formula (I) where R₁ and/or R₂=alkyl can be prepared by reductive alkylation using an aldehyde or ketone in the presence of a reducing agent such as formic acid, sodium cyanoborohydride or sodium triacetoxyborohydride.

Reaction Scheme 2

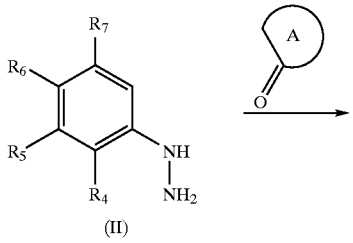

If, in any of the other processes mentioned herein, the substituent groups R₁, R₂, R₃, R₄, R₅, R₆ or R₇ is other than the one required, the substituent group may be converted to the desired substituent by known methods. The substituents R₁, R₂, R₃, R₄, R₅, R₆ or R₇ may also need protecting against the conditions under which the reaction is carried out. In such a case, the protecting group may be removed after the reaction has been completed.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt may be obtained by dissolving the free base in a suitable organic solvent and treating the solution with an acid, in accordance with conventional procedures for preparing acid addition salts from basic compounds.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylnethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilising and/or dispersing agents.

Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressured aerosol, the dosage unit may be determined by providing a valve to deliver a metered amount. The pressurized container or nebulizer may contain a solution or suspension of the active compound. Capsules and cartridges (made, for example, from gelatin) for use in an inhaler or isufflator may be formulated containing a powder mix of a compound of the invention and a suitable powder base such as lactose or starch.

A proposed dose of the active compounds of the invention for oral parenteral or buccal administration to the average adult human for the treatment of the conditions referred to above (e.g., obesity) is 0.1 to 500 mg of the active ingredient per unit dose which could be administered, for example, 1 to 4 times per day.

The invention will now be described in detail with reference to the following examples. It will be appreciated that the invention is described by way of example only and modification of detail may be made without departing from the scope of the invention.

EXPERIMENTAL

Assay Procedures

1. Binding to Serotonin Receptors

The binding of compounds of formula (I) to serotonin receptors was determined in vitro by standard methods. The preparations were investigated in accordance with the assays given hereinafter.

Method (a): For the binding to the 5-$HT_{2C}$ receptor the 5-$HT_{2C}$ receptors were radiolabelled with [$^3$H]-5-HT. The affinity of the compounds for 5-$HT_{2C}$ receptors in a CHO cell line was determined according to the procedure of D. Hoyer, G. Engel and H.O. Kalkman, *European J. Pharmacol.*, 1985, 118, 13–23.

Method (b): For the binding to the 5-$HT_{2B}$ receptor the 5-$HT_{2B}$ receptors were radiolabelled with [$^3$H]-5-HT. The affinity of the compounds for human 5-$HT_{2B}$ receptors in a CHO cell line was determined according to the procedure of K. Schmuck, C. Ullmer, P. Engels and H. Lubbert, *FEBS Lett.*, 1994, 342, 85–90.

Method (c): For the binding to the 5-$HT_{2A}$ receptor the 5-$HT_{2A}$ receptors were radiolabelled with [$^{125}$I]-DOI. The affinity of the compounds for 5-$HT_{2A}$ receptors in a CHO cell line was determined according to the procedure of D. J. McKenna and S. J. Peroutka, *J. Neurosci.*, 1989, 9/10, 3482–90.

The thus determined activity of compounds of formula (I) is shown in Table 1.

TABLE 1

| | Radioligand Binding Data | | |
|---|---|---|---|
| Compound | $K_i(2C)$/nM | $K_i(2A)$/nM | $K_i(2B)$/nM |
| Example 1 | 65 | 122 | 40 |
| Example 11 | 63 | 314 | 210 |
| Example 14 | 64 | 375 | 180 |
| Example 26 | 106 | 144 | 127 |
| Example 27 | 141 | 545 | 496 |
| Example 29 | 474 | 823 | 653 |
| Example 30 | 19 | 48 | 31 |
| Example 31 | 65 | 550 | 161 |
| Example 32 | 27 | 106 | 58 |
| Example 33 | 63 | 233 | 152 |
| Example 37 | 41 | 86 | 65 |
| Example 43 | 62 | 167 | 162 |

2. Functional Activity

The functional activity of compounds of formula (I) was assayed using a Fluorimetric Imaging Plate reader (FLIPR) in the following manner.

CHO cells expressing either the h5-$HT_{2C}$ or h5-$HT_{2A}$ receptors were counted and plated into standard 96 well microtitre plates before the day of testing to give a confluent monolayer. The following day the cells were dye loaded with the calcium sensitive dye Fluo 3-AM by incubation with serum free culture maintenance media containing pluronic acid and Fluo 3-AM dissolved in DMSO at 37° C. in a $CO_2$ incubator at 95% humidity for approximately 90 minutes. Unincorporated dye was removed by washing with Hanks balanced salt solution containing 20 mM HEPES and 2.5 mM probenecid (the assay buffer) using an automated cell washer to leave a total volume of 100 $\mu$L/well.

The drug (dissolved in 50 $\mu$L of assay buffer) was added at a rate of 70 $\mu$L/sec to each well of the FLIPR 96 well plate during fluorescence measurements. The measurements are taken at 1 sec intervals and the maximum fluorescent signal was measured (approx 10–15 secs after drug addition) and compared with the response produced by 10 $\mu$M 5-HT (defined as 100%) to which it is expressed as a percentage response (relative efficacy). Dose response curves were constructed using Graphpad Prism (Graph Software Inc.).

The thus determined activity of compounds of formula (I) is shown in Table 2.

TABLE 2

Functional Data

| Compound | EC$_{50}$ (nM) | h5-HT$_{2A}$ Relative Efficacy (%) | EC$_{50}$ (nM) | h5-HT$_{2C}$ Relative Efficacy (%) |
|---|---|---|---|---|
| Example 1 | 10000 | 0 | 272 | 77 |
| Example 2 | 10000 | 0 | 347 | 85 |
| Example 4 | 10000 | 60 | 179 | 65 |
| Example 11 | 1686 | 25 | 89 | 85 |
| Example 14 | 6247 | 48 | 252 | 80 |
| Example 15 | 10000 | 0 | 1732 | 93 |
| Example 16 | 10000 | 0 | 307 | 86 |
| Example 18 | 2102 | 63 | 36 | 75 |
| Example 30 | 361 | 43 | 90 | 72 |
| Example 33 | 10000 | 22 | 316 | 81 |
| Example 36 | 1339 | 25 | 189 | 64 |
| Example 37 | 2990 | 28 | 127 | 84 |
| Example 42 | 805 | 51 | 87 | 74 |

SYNTHETIC EXAMPLES

Example 1

(S)-1-(7,8-Difluoro-1,2,3,4-tetrahydrocyclopent[b]indol-4-yl2-propylamine fumarate

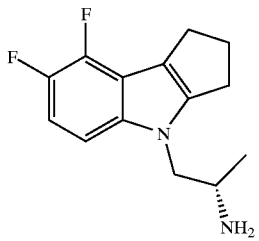

2'-Bromo2,2,2-trfluoroacetanilide
To a stirred solution of 2-bromo-4,5-difluoroaniline [H. Ishikawa, T. Uno, H, Miyamoto, H. Hiraki, H. Tamaoka, M. Tominaga and K. Nakagawa, Chem. Pharm. Bull., 1990, 38(9), 2459–2462] (72 g, 34 mmol) in ether (50 mL) at 0° C. was added sodium carbonate (5.4 g, 44 mmol) and trifluoroacetic anhydride (6.2 mL, 44 mmol). The reaction mixture was stirred at room temperature for 1 h. Water (100 mL) was added and the mixture was extracted with dichloromethane (3×100 mL). The organic extracts were combined, dried (magnesium sulfate), filtered and concentrated in vacuo to give the product (9.9 g, 94%) as a white solid. IR $v_{max}$ (Nujol)/cm$^{-1}$ 3270, 1716, 1550, 1489, 1465, 1226, 1181, 919, 876 and 821; NMR $\delta_H$ (400 MHz, CDCl$_3$) 7.45–7.5 (1H, dd, J 7.5 Hz), 8.28–8.34 (1H, dd, J 8 Hz) and 8.36 (1H, br s).
7,8-Difluoro-1,2,3,3a,4,8a-hexahydro-8a-hydroxy-cyclopent[b]indole
A stirred solution of 2'-Bromo-2,2,2-trifluoroacetanilide (5.3 g, 35 mmol), in tetrahydrofuran (200 mL) was cooled to −78° C. A solution of methyllithium (12.5 ml, 35 mmol, 1.4 M in ether) was added maintaining the temperature of reaction below −75° C. After 10 min a solution of tert-butyllithium (20.5 mL, 70 mmol, 1.7 M in pentane) was added over 5 min and the reaction was stirred for 1 h at −78° C. The mixture was warmed to −50° C. and 2-chlorocyclopentanone (2.1 mL, 42 mmol) was added dropwise. The reaction was warmed slowly to room temperature and stirred for a further 2 h. A solution of potassium hydroxide in methanol (10%, 20 mL) was added and the mixture was stirred at room temperature for 12 h. The mixture was poured onto dilute hydrochloric acid (5%, 150 mL) and washed with dichloromethane (3×150 mL). The aqueous layer was basified (15% aqueous sodium hydroxide solution) and extracted with dichloromethane (3×150 mL). The organic extracts were combined, dried (magnesium sulfate), filtered and concentrated in vacuo to give the product (0.85 g, 11%) as a pale brown solid. R$_f$ 0.39 [SiO$_2$; heptane-ethyl acetate (10:3)]; NMR $\delta_H$ (400 MHz, CDCl$_3$) 1.53–1.67 (2H, m), 1.78–1.89 (1H, m), 2.02–2.17 (2H, m), 2.29–2.37 (1H, m), 4.04 (1H, dd, J 6 Hz), 6.21–6.26 (1H, m) and 6.86–6.94 (1H, m).
7,8-Difluoro-1,2,3,4-tetrahydrocyclopent[b]indole
A stirred solution of 7,8-difluoro-1,2,3,3a,4,8a-hexahydro-8a-hydroxy-cyclopent[b]indole (1.1 g, 5.2 mmol), in dichloromethane (150 mL) was cooled to 0° C. Trifluoroacetic acid (20 drops) was added and the reaction mixture was stirred at room temperature for 18 h. The reaction mixture was poured onto saturated sodium hydrogen carbonate solution (20 mL) and extracted with dichloromethane (3×50 mL). The organic extracts were combined, dried (magnesium sulfate), filtered, concentrated in vacuo and purified by column chromatography [SiO$_2$; ethyl acetate-heptane (1:5)]to give the product (0.78 g, 78%) as a white crystalline solid. IR $v_{max}$ (Nujol)/cm$^{-1}$ 3467, 2925, 2854, 1565, 1515, 1450, 1348, 1327, 1244, 1053, 1025, 977, 857, 783, 630 and 516; NMR $\delta_H$ (400 MHz, CDCl$_3$) 2.49–2.58 (2H, m), 2.79–2.87 (2H, m), 2.9–2.96 (2H, m), 6.81–6.95 (2H, m), and 7.83 (1H, br s).
(S)-4-[2-(tert-Butoxyarbonylamino)propyl]-7,8-difluoro-1,2,3,4-tetrahydrocyclopent[b]indole
7,8-Difluoro-1,2,3,4-tetrahydrocyclopent[b]indole (0.56 g, 2.9 mmol) was added portionwise to a mixture of methyl sulfoxide (15 mL) and crushed potassium hydroxide (0.57 g, 10.2 mmol). The mixture was warmed to 35° C. and stirred for 30 min. A solution of (S)-2-(tert-butoxycarbonylamino)propane methanesulfonate (1.85 g, 7.3 mmol) in methyl sulfoxide (5 mL) was added over a 1 h period, the mixture was then stirred at 35° C. for 20 h. Water (30 mL) was added and the mixture was extracted with ether (3×50 mL). The organic extracts were combined, dried (magnesium sulfate), filtered, concentrated in vacuo and purified by column chromatography [SiO$_2$; heptane-ethyl acetate (5:1)] to give the product (0.55 g, 52%) as a white crystalline solid; IR $v_{max}$ (Nujol)/cm$^{-1}$ 3366, 1684, 1516, 1456, 1248, 1022 and 773; NMR $\delta_H$ (400 MHz, CDCl$_3$) 1.1 (3H, d, J 7 Hz), 1.43 (9H, br s), 2.48–2.57 (2H, m), 2.79–2.87 (2H, m), 2.91–2.98 (2H, m), 3.84–3.92 (1H, dd, J 7 Hz), 3.96–4.07 (1H, m), 4.08 (1H, br s), 4.4 (1H, br s), 6.83–6.92 (1H, m) and 6.94–7.08 (1H,brs).
(S)-1-(7,8-Difluoro-1,2,3,4-tetrahydrocyclopent[b]indol-4-yl)-2-propylamine fumarate
A solution of (S)-4-[2-(tert-butoxycarbonylamino)propyl]-7,8-difluoro-1,2,3,4-tetrahydrocyclopent[b]indole (0.4 g, 1.1 mmol) and trifluoroacetic acid (5 mL) in dichloromethane (15 mL) was stirred at room temperature for 1 h. The mixture was made basic by the addition of aqueous sodium hydroxide solution (2 N), then extracted with dichloromethane (3×50 mL). The organic extracts were combined, dried (magnesium sulfate), filtered and concentrated in vacuo to give an orange oil. The oil was dissolved in 2-propanol (5 mL) and the solution was heated to boiling then fumaric acid (0.38 g, 3.3 mmol) was added. The mixture was cooled to room temperature and filtered The filter-cake was washed (2-propanol, ether) and dried in vacuo to give the title compound (0.89 g, 68%) as a pale orange solid. mp. 154–156° C. (dec.); NMR $\delta_H$ (400 MHz, DMSO-d$_6$) 1.13 (3H, d, J 7 Hz), 2.43–2.52 (2H, m), 2.78–2.94 (4H, m), 3.5–3.57 (1H, m), 4.13 (1H, d, J 8 Hz), 4.29 (1H, dd, J 6.5 Hz), 6.55 (2H, s), 7.01–7.10 (1H, m) and 7.26–7.31 (1H, m).

Reference herein to (S)-1-(7,8-Difluoro-1,2,3,4-tetydrocyclopent[b]indol-4-yl)-2-propylamine fumarate will be understood to mean a compound prepared by the above synthetic procedure.

Other compounds of formula (I) a defined herein may be prepared according to the following synthetic methods.

Phenylhydrazine Preparation (General Method A)

Commercially available substituted phenylhydrazines were used with the exception of the compounds listed below in Table 3. The compounds listed in Table 3 were synthesised in accordance with the method (general synthetic method A) given below for compounds 36a, 37a and 42a.

Compounds 36a, 37a and 42a: 4-Fluoro-3-methoxyphenylhydrazine hydrochloride

To stirred hydrochloric acid (100 mL) at 0° C. was added 3-methoxy-4-fluoroaniline (10 g, 71 mmol) followed by water (10 mL) and more hydrochloric acid (10 mL). The mixture was warmed to room temperature, stirred for 20 min then cooled to −5° C. A solution of sodium nitrite (5.14 g, 75 mmol) in water (25 mL) was added dropwise such that the internal temperature remained below 0° C. The mixture was warmed to room temperature and stirred for 2 h. The mixture was cooled to −5° C. and a solution of tin(II) chloride dihydrate (64 g, 284 mmol) in hydrochloric acid (200 mL) was added dropwise such that the internal temperature remained below 0° C. The mixture was warmed to room temperature, stirred for 3 h then filtered. The filter cake was washed with hydrochloric acid and dried under vacuum to give a pink solid (7.4 g). The precipitate from the combined filtrates was filtered-off, washed (hydrochloric acid) and dried under vacuum to give a further crop of product (1.8 g. to give a combined yield of 9.2 g, 67%). Data for 4-fluoro3-methoxyphenylhydrazine hydrazine hydrochloride are included in Table 3 below.

TABLE 3

Phenylhydrazines (prepared by General Method A)

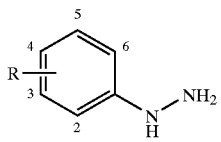

In this structural formula there may be a plurality of R groups, as detailed in Table 3 below.

| Compound | R | Yield | Data |
|---|---|---|---|
| 23a | 3-OBn | 72% | Hydrochloride. NMR (400 MHz, CDCl$_3$) $\delta_H$ 7.43 (2H, d, J 7.5 Hz), 7.38 (2H, t, J 7.5 Hz), 7.32 (1H, t, J 7 Hz), 7.13 (1H, t J 8 Hz), 6.48 (1H, t, J 2.5 Hz), 6.45 (1H, dd, J 8, 2.5 Hz), 6.41 (1H, dd, J 8, 2.5 Hz), 5.04 (2H, s); HPLC [Supelcosil ABZ+; 1.0 ml/min, methanol-10 mM aqueous ammonium acetate solution (80:20)] 90% (2.62 min). |
| 24a | 3-O$^i$Pr | 52% | Hydrochloride. NMR (400 MHz, DMSO-d$_6$) $\delta_H$ 10.24 (3H, br s, NH$_3$), 8.26 (1H, br s, NH), 7.16 (1H, t, J 8.2 Hz), 6.61 (1H, t, J 2.1 Hz), 6.54 (1H, dd, J 8.0, 1.6 Hz), 6.50 (1H, dd, J 8.3, 2.0 Hz), 4.57 (1H, quint, J 6.0 Hz), 1.27 (6H, d, J 6.0 Hz); HPLC: [Supelcosil ABZ+; 1.0 ml/min, methanol-10 mM aqueous ammonium acetate solution (80:20)] 90% (2.55 min). |
| 25a | 3-O$^i$Pr | as 24a | as Compound 24a |
| 28a | 2-OCF$_3$ | 77% | Hydrochloride. NMR (400 MHz, DMSO-d$_6$) $\delta_H$ 10.56 (3H, br s, NH$_3$), 8.41 (1H, br s, NH), 7.37–7.31 (3H, m), 7.03 (1H, dq, J 8.6, 4.3 Hz); HPLC: [Supelcosil ABZ+; 1.0 ml/min, methanol-10 mM aqueous ammonium acetate solution (80:20)] 99% (2.38 min). |
| 29a | 4-OCF$_3$ | 84% | m.p. 216° C.; Found: C, 34.04; H, 3.42; N, 11.11%. C$_7$H$_7$F$_3$N$_2$O.1.5H$_2$O requires: C, 34.06; H, 3.47; N, 11.35%. |
| 33a | 3,4-di-F | 70% | NMR (400 MHz, CDCl$_3$) $\delta_H$ 3.56 (2H, br s), 5.13 (1H, br s), 6.47 (1H, m), 6.69 (1H, m), 6.99 (1H, dd, J 8.53 Hz, 17.57 Hz); IR v$_{max}$ (nujol)/cm$^{-1}$ 3258, 1613, 1516, 1465, 1265, 1222 and 771. |
| 36a | 4-F, 3-OMe | 67% | m.p. 250+° C. (dec.); NMR: (400 MHz, DMSO-d$_6$) $\delta_H$ 10.17 (3H, s, NH$_3$), 8.14 (1H, s, NH), 7.15 (1H, dd, J 11.6, 8.6 Hz), 6.95 (1H, dd, J 7.6, 3.0 Hz), 6.54 (1H, dt, J 8.6, 3.0 Hz), 3.83 (3H, s, MeO). |
| 37a | 4-F, 3-Ome | as 36a | as Compound 36a |
| 42a | 4-F, 3-Ome | as 36a | as Compound 36a |

Fischer Synthesis of Indoles (General Method B)

The indoles listed in Table 4 below were synthesised in accordance with the following synthetic methods (General Methods B(i) and B(ii)) given below for compounds 14b, 30b, 11b and 12b.

Method B(i): Aqueous Sulfuric Acid

Compounds 14b and 30b: 1,2,3,4-Tetrahydrocyclopent[b]indole

A solution of phenylhydrazine (32.44 g, 300 mmol) in 2-propanol (300 mL) was treated with cyclopentanone (27 mL, 25.7 g, 305 mmol). The solution was stirred at 20° C. for 1 h and poured onto a mixture of ice (900 g) and water (300 mL). The chilled mixture was stirred until the ice melted and then filtered. The filter-cake was washed with water (2×300 mL) to give an off-white, moist solid (85 g). The solid was added to water (540 mL) and the stirred suspension was treated with concentrated sulfuric acid (33 mL, 61 g, 600 mmol). The suspension was then heated under reflux for 30 min, cooled to 0° C. and then stirred for 15 min. The dark-red solid was filtered off, washed with water (2×60 mL) and air-dried for 18 h The crude product was added to stirred dichloromethane (300 mL), stirred for 30 min and filtered. The tarry residue was washed with dichloromethane (100 mL) and the filtrate was treated with silica (48 g), stirred for 1 h and filtered. The silica residue was washed with dichloromethane (400 mL) and the filtrate was concentrated to give a solid, which was triturated with hexane to give 1,2,3,4-tetrahydrocyclopent[b]indole (30 g, 65%) as a pink solid. Analytical data for 1,2,3,4-tetrahydrocyclopent[b]indole are included in Table 4 below.

Where the intermediate hydrazone was obtained as an oil the following method was used:

A solution of the arylhydrazine (100 mmol) in benzene (100 mL) was treated with cyclopentanone (9 mL, 8.6 g, 102 mmol). The solution was heated under reflux with azeotropic removal of water for 30–60 min. The solution was allowed to cool and was concentrated in vacuo to give the arylhydrazone as an oil which was used directly in the subsequent step as described above.

Method B(d): Ethanol as Solvent
Compounds 11b and 12b: 1,2,3,4-Tetrahydro-6methoxy-cyclopent[b]indole and 1,2,3,4-tetrahydro-8-methoxycyclopent[b]indole To stirred, degassed ethanol (20 mL), shielded from light and under an atmosphere of Ar at ambient temperature, was added 3-methoxyphenylhydrazine hydrochloride (1.0 g, 5.6 mmol) and cyclopentanone (0.5 mL, 5.7 mmol). The mixture was heated at reflux for 24 h, cooled to room temperature then poured onto 300 mL ice-water and made basic with saturated aqueous sodium bicarbonate solution (to pH 8). The suspension was filtered, and the resultant solid was washed with water and dried to afford the crude product as a dark brown solid (0.95 g, 89%) which was purified by flash column chromatography [$SiO_2$; isohexane-dichloromethane (3:2→1:1)] afforded the separated isomeric indole products. Alternatively the crude product was purified by filtration of a dichloromethane solution through a plug of silica and concentration in vacuo followed by trituration with toluene, filtration, and washing of the resultant solid with ice-cold toluene-heptane (1:1) to afford exclusively the 6-isomer. Analytical data for 1,2,3,4-tetrahydro-6-methoxy-cyclopent[b]indole and 1,2,3,4-tetrahydro-8-methoxy-cyclopent[b]indole are included in Table 4 below.

For the appropriate examples, pentindole regioisomers arising from the use of unsymmetrical arylhydrazines were separated by column chromatography, recrystallisation from toluene, cyclohexane, isohexane or ethanol or by trituration with toluene or pentane.

Table 4: Indoles Formed using General Methods B(i) and B(ii)

In this structural formula, there may be an additional double bond in the 5- or 6-membered ring fused to the indole ring. In Table 4 below, the substituents $R_4$ to $R_7$ are hydrogen unless otherwise stated in column 2.

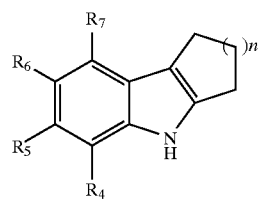

| Compound | Substitution Pattern (method) | n | Yield | Data |
|---|---|---|---|---|
| 2b | $R_6$ = F (i) | 1 | 67% | m.p. 102–103° C. (Ethanol); Found: C, 75.36; H, 5.80; N, 7.97%. $C_{11}H_{10}FN$ requires: C, 75.41; H, 5.75; N, 7.99%. |
| 3b | $R_5$ = Cl (i) | 2 | 18% | m.p. 181° C. (Ethanol); Found: C, 70.03; H, 5.87; N, 6.85%. $C_{12}H_{12}ClN$ requires: C, 70.07; H, 5.88; N, 6.81%. |
| 4b | $R_7$ = Cl (i) | 1 | 23% | Low-melting solid from mother liquors of 6-chloro isomer recrystallisation. NMR (400 MHz, $CDCl_3$) $\delta_H$ 7.88(1H, m, NH), 7.16(1H, dd, J 1, 8 Hz), 7.03(1H, dd, J 1, 8 Hz), 6.96 (1H, t, J 8 Hz), 3.04(2H, tt, J 1.5, 7 Hz), 2.85 (2H, tt, J 1.5, 7 Hz), 2.53(2H, quint, J 7 Hz); HPLC: [Supelcosil ABZ+; 1.0 mL/min, methanol-10 mM aqueous ammonium acetate solution (80:20)] 80% (8.00 min) + 6-chloro isomer (20%). |
| 5b | $R_5$ = Cl (i) | 1 | 21% | m.p. 188–191° C. (Ethanol); Found: C, 69.21; H, 5.18; N, 7.31% $C_{11}H_{10}ClN$ requires: C, 68.94; H, 5.26; N, 7.30%. |
| 6b | $R_5$ = Cl; synthetic method is (ii); n in the above formula is not applicable; the compound contains an S-heteroatom: 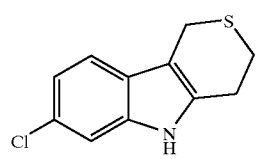 | | 37% | m.p. 179–182° C. (Ethanol); Found: C, 59.29; H, 4.44; N, 6.28; S, 14.38; Cl, 16.04%. $C_{11}H_{10}ClNS$ requires: C, 59.06; H, 4.51; N, 6.26; S, 14.33; Cl, 15.85%. |
| 7b | $R_5$ = Br (i) | 1 | 12% | m.p. 199.5–200° C. (dec.); Found: C, 55.48; H, 4.21; N, 5.85%. $C_{11}H_{10}BrN \cdot 0.125H_2O$ requires: C, 55.43; H, 4.33; N, 5.86%. |
| 8b | $R_5$ = Br (i) | 2 | 3.4% | NMR (400 MHz, $CDCl_3$) $\delta_H$ 7.67(1H, m, NH), 7.41(1H, d, J 1.5 Hz), 7.30(1H, d, J 8.5 Hz), |

-continued

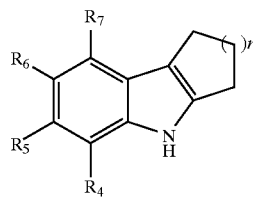

| Compound | Substitution Pattern (method) | n | Yield | Data |
|---|---|---|---|---|
|  |  |  |  | 7.16(1H, dd, J 1.5, 8.5 Hz), 2.73–2.64(4H, m), 1.95–1.82(4H, m); HPLC: [Supelcosil ABZ+ 1.0 ml/min, methanol-10 mM aqueous ammonium acetate solution (80:20)] 99% (10.12 min). |
| 9b | $R_6$ = Cl (i) | 2 | 35% | NMR (400 MHz, CDCl$_3$) $\delta_H$ 7.67(1H, m, NH), 7.40(1H, d, J 2 Hz), 7.16(1H, d, J 8.5 Hz), 7.04(1H, dd, J 2, 8.5 Hz), 2.74–2.69(2H, m), 2.67–2.63(2H, m), 1.94–1.82(4H, m); HPLC: [Supelcosil ABZ+ 1.0 ml/min, methanol-10 mM aqueous ammoniun acetate solution (80:20)] 99% (9.28 min). |
| 10b | $R_6$ = Cl (i) | 1 | 42% | NMR (400 MHz, CDCl$_3$) $\delta_H$ 7.84(1H, m, NH), 7.39(1H, d, J 2 Hz), 7.19(1H, d, J 8.5 Hz), 7.03(1H, dd, J 8.5, 2 Hz), 2.86(2H, m), 2.79 (2H, tt, J 6.5, 1.5 Hz); HPLC: [Supelcosil ABZ+ 1.0 ml/min, methanol-10 mM aqueous ammonium acetate solution (80:20)] 99% (7.67 min). |
| 11b | $R_5$ = OMe (ii) | 1 | 30% | m.p. 136–137.5° C.; NMR (400 MHz, CDCl$_3$) $\delta_H$ 7.68(1H, m, NH), 7.29(1H, d, J 8.5 Hz), 6.81(1H, d, J 2 Hz), 6.74(1H, dd, J 2, 8.5 Hz), 3.83(3H, s), 2.85–2.76(4H, m), 2.55–2.47(2H, m). |
| 12b | $R_7$ = OMe (ii) | 1 |  | m.p. 87–89° C.; NMR (400 MHz, CDCl$_3$) $\delta_H$ 7.79(1H, m, NH), 6.99(1H, t, J 8 Hz), 6.91 (1H, dd, J 8, 1 Hz), 6.49(1H, d, J 8 Hz), 3.90 (3H, s), 2.98–2.93(2H, m), 2.84–2.78(2H, m), 2.55–2.47(2H, m). |
| 13b | $R_4$ = $R_5$ = Cl (i) | 1 | 28% | m.p. 104–107° C. (isohexane); Found: C, 58.65; H, 4.04; N, 6.20; Cl, 31.30%. C$_{11}$H$_9$Cl$_2$N requires: C, 58.43; H, 4.01; N, 6.19; Cl, 31.36%. |
| 14b | (i) | 1 | 65% | m.p. 107–108° C. (hexane); Found: C, 83.04; H, 7.12; N, 8.78%. C$_{11}$H$_{11}$N.0.1H$_2$O requires: C, 83.09; H, 7.10; N, 8.81%. |
| 15b | $R_5$ = $R_7$ = Cl; synthetic method is (ii); n in the above formula is not applicable; the compound contains an S-heteroatom: | | 7% | (Synthesised using tetraydrothiophen-3-one, initial product aromatises during reaction) m.p. 105° C. (heptane); NMR (400 MHz, CDCl$_3$) $\delta_H$ 8.20(1H, m, NH), 7.44(1H, d, J 5.5 Hz), 7.26 (1H, d, J 1.5 Hz), 7.17(1H, d, J 1.5 Hz), 7.03 (1H, d, J 5.5 Hz); HPLC: [Supelcosil ABZ+ 1.0 ml/min, methanol-10 mM aqueous ammonium acetate solution (90:10)] 99% (6.66 min). |

| Compound | Substitution Pattern (method) | n | Yield | Data |
|---|---|---|---|---|
| 16b | $R_5$ = Cl; $R_6$ = F (i) | 1 | 21% | m.p. 139.5–140° C. (cyclohexane); Found: C, 62.87; H, 4.35; N, 6.69%. C$_{11}$H$_9$ClFN requires: C, 63.02; H, 4.33; N, 6.68%. |
| 17b | $R_5$ = CF$_3$ (i) | 1 | 33% | m.p. 161–162° C. (pentane); Found: C, 63.87; H, 4.46; N, 6.18%. C$_{12}$H$_{10}$FN requires: C, 64.00; H, 4.48; N, 6.22%. |
| 18b | $R_7$ = Cl; $R_6$ = F (i) | 1 | 40% | Low-melting solid. NMR (400 MHz, CDCl$_3$) $\delta_H$ 7.86(1H, m, NH), 7.07(1H, dd, J 3.5, 9 Hz), 6.86(1H, t, J 9 Hz), 3.03(2H, tt, J 1.5, 7 Hz), 2.84(2H, t, J 7 Hz) and 2.53(2H, quintet, J 7 Hz); HPLC: [Xterra; 2.0 ml/min, methanol- |

-continued

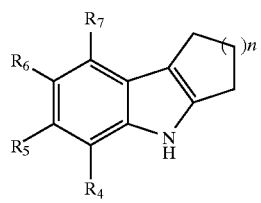

| Compound | Substitution Pattern (method) | n | Yield | Data |
|---|---|---|---|---|
| | | | | 10 mM aqueous ammonium acetate solution (80:20)] 99.5% (8.29 min). |
| 19b | $R_5 = R_6 = Cl$ (i) | 1 | 12% | m.p. 169° C. (Toluene); Found: C, 58.45; H, 3.95; N, 6.19%. $C_{11}H_9Cl_2N$ requires: C, 58.43; H, 4.01; N, 6.19%. |
| 20b | $R_6 = OMe$ (i*) | 1 | 85% | (*as method (i) but at room temperature and in water). NMR (400 MHz, $CDCl_3$) $\delta_H$ 7.71(1H, m, NH), 7.18(1H, d, J 8.5 Hz), 6.91(1H, d, J 2.5 Hz), 6.74(1H, dd, J 8.5, 2.5 Hz), 3.85(3H, s), 2.87–2.78(4H, m), 2.56–2.49(2H, m); HPLC: [Supelcosil ABZ+; 1.0 ml/min, methanol-10 mM aqueous ammonium acetate solution (80:20)] 94% (3.81 min). |
| 21b | $R_7 = CF_3$ (i) | 1 | 50% | NMR (400 MHz, $CDCl_3$) $\delta_H$ 8.05(1H, m, NH), 7.44(1H, d, J 8 Hz), 7.37(1H, d, J 8 Hz), 7.12 (1H, t, J 8 Hz), 2.95–2.87(4H, m), 2.60–2.50 (2H, m); HPLC: [Supelcosil ABZ+; 1.0 ml/min, methanol-10 mM aqueous ammonium acetate solution (80:20)] 99% (6.63 min). |
| 22b | $R_6 = R_7 = Cl$ (i) | 1 | 6% | (Mixture with 7,8-dichloro product). m.p. 107–114° C.; HPLC: [Supelcosil ABZ+; 1.0 ml/min, methanol-10 mM aqueous ammonium acetate solution (80:20)] 50% (12.25 min). |
| 23b | $R_7 = OBn$ (ii) | 1 | 10% | NMR (400 MHz, $CDCl_3$) $\delta_H$ 7.79(1H, m, NH), 7.50(2H, d, J 7.5 Hz), 7.38(2H, t, J 7.5 Hz), 6.97(1H, t, J 8 Hz), 6.93(1H, dd, J 8, 1 Hz), 6.56(1H, dd, J 8, 1 Hz), 5.18(2H, s), 3.01(2H, t, J 7 Hz), 2.83(2H, t, J 7 Hz), 2.52(2H, quint., J 7 Hz); HPLC: [Supelcosil ABZ+; 1.0 ml/min, methanol-10 mM aqueous ammonium acetate solution (80:20)] 97% (9.24 min). |
| 24b | $R_7 = O^iPr$ (ii) | 1 | 4% | NMR (400 MHz, $CDCl_3$) $\delta_H$ 7.74(1H, br s, NH), 6.94(1H, t, J 7.8 Hz), 6.88(1H, dd, J 8.2, 0.9 Hz), 6.50(1H, d, J 6.9 Hz), 4.57(1H, quint, J 6.0 Hz), 2.93(2H, obs tt, J 6.9, 1.5 Hz), 2.80 (2H, obs tt, J 6.5, 1.5 Hz), 2.52–2.45(2H, m), 1.34(6H, d, J 6.0 Hz); HPLC: [Supelcosil ABZ+; 1.0 ml/min, methanol-10 mM aqueous ammonium acetate solution (80:20)] 77% (4.87 min), material decomposes under mildly acidic conditions. |
| 25b | $R_5 = O^iPr$ (ii) | 1 | 2% | MS [Found: (m/z) 215. $C_{14}H_{17}NO$ requires: $M^+$ 215]; HPLC: [Supelcosil ABZ+, 1.0 ml/min, methanol-10 mM aqueous ammonium acetate solution (80:20)] 40% (4.62 min), material decomposes under mildly acidic oxygenated conditions. |
| 26b | $R_5 = R_7 = Cl$ (i) | 1 | 51% | m.p. 61–62° C. (hexane); Found: C, 58.28; H, 3.99; N, 6.28%. $C_{11}H_9Cl_2N$ requires: C, 58.43; H, 4.01; N, 6.19%. |
| 28b | $R_4 = OCF_3$ (i) | 1 | 55% | NMR (400 MHz, $CDCl_3$) $\delta_H$ 8.07(1H, br s, NH), 7.32(1H, d, J 7.5 Hz), 7.01(1H, t, J 7.6 Hz), 6.96(1H, dt, J 7.6, 1.3 Hz), 2.86(2H, obs dd, J 7.9, 6.3 Hz), 2.80(2H, obs tt, J 7.9, 1.5 Hz), 2.57–2.50(2H, m); HPLC: [Supelcosil ABZ+; 1.0 ml/min, methanol-10 mM aqueous ammonium acetate solution (80:20)] 99% (6.11 min). |
| 29b | $R_6 = OCF_3$ (i) | 1 | 89% | NMR (400 MHz, $CDCl_3$) $\delta_H$ 7.89(1H, m, NH), 7.27(1H, m), 7.23(1H, d, J 8.5 Hz), 6.95(1H, dd, J 9, 2 Hz), 2.86(2H, t, J 7 Hz), 2.81(2H, t, J 7 Hz), 2.53(2H, quint., J 7 Hz); HPLC: [Supelcosil ABZ+; 1.0 ml/min, methanol- |

-continued

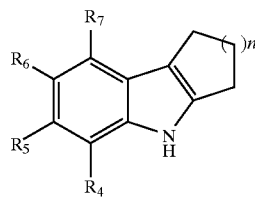

| Compound | Substitution Pattern (method) | n | Yield | Data |
|---|---|---|---|---|
| 30b | (i) | 1 | as 14b | 10 mM aqueous ammonium acetate solution (80:20)] 99% (6.87 min). as Compound 14b |
| 31b | $R_5 = F$ (i) | 1 | 10% | m.p. 128–131° C. (cyclohexane); Found: C, 75.39; H, 5.80; N, 7.98%. $C_{11}H_{10}FN$ requires: C, 75.41; H, 5.75; N, 7.99%. |
| 32b | Synthetic method is (i); N in the above formula is not applicable; the compound contains an S-heteroatom: | | 26% | m.p. 153° C. (dec.); Found: C, 67.97; H, 5.08; N, 7.90%. $C_{10}H_9NS.0.1H_2O$ requires: C, 67.84; H, 5.24; N, 7.91%. |

![S-heteroatom structure]

| 33b | $R_5 = R_6 = F$ (ii) | 1 | 52% | Mixture of inseparable regioisomers, used without further purification. |
| 34b | $R_7 = Cl$, $R_6 = Me$ (i) | 1 | 25% | Low-melting solid; NMR (400 MHz, CDCl$_3$) $\delta_H$ 7.61(1H, m, NH), 6.97(1H, d, J 8 Hz), 6.87 (1H, d, J 8 Hz), 3.01(2H, tt, J 1.5, 7 Hz), 2.75 (2H, tt, J 1.5, 7 Hz), 2.47(2H, m) and 2.41 (3H, s). HPLC: [Supelcosil ABZ+; 1.0 ml/min, methanol-10 mM aqueous ammonium acetate solution (80:20)] 90% (8.90 min) [and 6-chloro-7-methyl 10% (8.54 min)]. |
| 35b | $R_7 = Cl$, $R_6 = Me$ (i) | 1 | as 34b | as Compound 34b |
| 36b | $R_6 = F$, $R_5 = OME$ (ii) | 1 | 44% | NMR (400 MHz, DMSO-d$_6$) $\delta_H$ 10.69(1H, s, NH), 7.08(1H, d, J 12.0 Hz), 6.98(1H, d, J 7.6 Hz), 3.83(3H, s, MeO), 2.79(2H, m), 2.69 (2H, t, J 7.0 Hz), 2.50(2H, m). |
| 37b | $R_6 = F$, $R_5 = OMe$ (ii) | 1 | as 36b | as Compound 36b |
| 39b | $R_5 = Cl$; $R_6 = F$ (i) | 1 | as 16b | as Compound 16b |
| 40b | $R_7 = Cl$ $R_6 = F$ (i) | 1 | as 18b | as Compound 18b |
| 41b | $R_7 = Br$ (i) | 1 | 37% | NMR (400 MHz, CDCl$_3$) $\delta_H$ 7.82(1H, s, NH), 7.19(1H, d, J 8 Hz), 7.16(1H, d, J 8 Hz), 6.89 (1H, t) J 8 Hz), 3.08–3.03(2H, m), 2.88–2.77 (2H, m), 2.55–2.46(2H, m); HPLC: [Supelcosil ABZ+; 1.0 ml/min, methanol-10 mM aqueous ammonium acetate solution (80:20)] 95% (2.33 min). |
| 42b | $R_6 = F$, $R_7 = OMe$ (ii) | 1 | — | Material obtained by column chromatography of the mother liquor from Examples 38b and 39b. The material was used immediately without further purification or analysis. |
| 43b | $R_4 = Cl$ (i) | 1 | 20% | m.p. 64–66° C. (Ethanol water); Found: C, 68.81; H, 5.24; N, 7.32%. $C_{11}H_{10}ClN$ requires: C, 68.94; H, 5.26; N, 7.30%. |
| 44b | $R_4 = Cl$ (i) | 1 | as 43b | as Compound 43b |

Compound 27b: 6Ethylthio-1,2,3,4-tetrahydrocyclopent[b]indole 1,2,3.4-Tetrahydro-6-(triisopropylsilyl)thio-cyclopent-[b]-indole Palladium dibenzylidene-acetone (0.155 g, 5 mol %) and tricyclohexylphosphine (0.19 g, 20 mol %), were weighed out into a flask pre-flushed with argon, and subsequently flushed with argon for 5 min before dissolution in toluene (20 mL). The deep red mixture was stirred at room temperature for 5 minutes under argon, then 6-bromo-1,2,3,4-tetrahydrocyclopent[b]indole (0.8 g, 3.4 mmol) was added in one portion. After a further 5 min a solution of potassium (triisopropylsilyl)sulfide (*Tetrahedron Letts.*, 1994, 35(20), 3221–3224 and 3225–6)) in tetrahydrofuran (6 mL) was added via syringe over 4 min The mixture was stirred for 45 min at room temperature, heated at 80° C. (bath temp) for 70 min then cooled to room temperature over 16 h. The mixture was partitioned between toluene (40 mL) and water (60 mL). The separated aqueous layer was extracted with toluene (30 mL) and the combined organic extracts were washed with brine (20 mL), dried ($Na_2SO_4$), filtered and concentrated in vacuo. The residue was purified by column chromatography [$SiO_2$; heptane-ethyl acetate (98:2) to (96:4)] to yield 1,2,3,4-tetrahydro-6-(triisopropylsilyl)thio cyclopent[b]indole as a pale yellow solid (0.85 g, 73%); NMR (400 MHz, $CDCl_3$) $\delta_H$ 7.76 (1H, br s, NH), 7.43 (1H, d, J 1.5 Hz), 7.27–7.25 (1H, m), 7.18 (1H, dd, J 8.2, 1.5 Hz), 2.85 (2H, obs dt, J 6.9, 1.6 Hz), 2.79 (2H, obs t, J 7.0 Hz), 2.52 (2H, obs quint, J 7.0 Hz), 1.29–1.19 (3H, m), 1.08 (18H, d, J 7.0 Hz); HPLC: [Supelcosil ABZ+; 1.0 ml/min, methanol-10 mM aqueous ammonium acetate solution, (90:10)] 99% (11.1 min).

6-Ethylthio-1,2,3,4-tetrahydrocyclopent[b]indole

A solution of 1,2,3,4-tetrthydro-6-triisopropylsilylthio-cyclopent-[b]-indole (439 mg, 1.31 mmol) and cesium fluoride (395 mg, 2.62 mmol) in dimethyl formamide was stirred at room temperature for 30 min. Iodoethane (0.21 mL, 2.62 mmol) was added dropwise to the suspension and the reaction was stirred at room temperature for 16 h. The reaction mixture was poured onto ice-water (50 mL) and then extracted with ethyl acetate (3×50 mL). The organic extracts were combined, dried (magnesium sulfate) and concentrated in vacuo. The residue was purified by column chromatography [$SiO_2$; heptane—ethyl acetate (5:1)] to afford the title compound (158 mg, 56%) as a white solid; NMR (400 MHz, $CDCl_3$) $\delta_H$ 1.26 (3H, t, J7.03Hz), 2.53 (2H, m), 2.78–2.93 (6H, m), 7.15 (1H, dd, J 1.51 Hz, 8.03Hz), 7.39 (1H, d, J 1.51Hz), 7.81 (1H, br s); IR $\nu_{max}$ (nujol)/$cm^{-1}$ 3403, 3382, 2925, 2854, 1456, 1376 and 808.

Indole Alkylation (General Method C)

The indoles prepared in accordance with the above synthetic methods may be alkylated in accordance with the general synthetic method (General Method C) given below for compound 30c. Table 5 gives details of the compounds prepared in this way Compound 30c: (R) 4-[2-(ter-Butoxycarbonylamino)propyl]-1,2,3,4-tetrahydrocyclopent[b]indole Methyl sulfoxide (40 mL) was warmed to 40° C. for 15 min and treated with powdered potassium hydroxide (85%, 2.64 g, 40 mmol). The suspension was stirred for 5 min and then 1,2,3,4-tetrahydrocyclopent[b]indole (1.57 g, 10 mmol) was added. The suspension was stirred at 40° C. for 60 min, then a solution of (R)tert-butyl [2-[(1-methanesulfonyl)oxy] propyl]carbamate (6.33 g, 25 mmol) in methyl sulfoxide (13 mL) was added dropwise in portions every 10 min over 90 min. The resultant suspension was stirred at 40° C. for 18 h and then cooled. Di-tert-butyl dicarbonate (2.3 mL, 2.2 g, 10 mmol) was added and the suspension was stirred for a further 2 h at 20° C. and poured onto a mixture of ice (165 g) and water (55 mL). The suspension was stirred for 1 h and then the crude product was filtered-off, washed with water (2×25 mL) and air-dried for 5 min [alternatively, the work-up employed ethyl acetate extraction and chromatography ($SiO_2$; ethyl acetate—dichloromethane (0:1→1:19)]. The crude product was dissolved in ethyl acetate, dried (magnesium sulfate) and concentrated to give a solid which was triturated with hexane to give the product as an off-white solid (2.34 g, 74%). Data for (R) 4-[2-(tert-butoxycarbonylamino)propyl]1,2,3,4-tetrahydrocyclopent[b]indole are listed in Table 5.

TABLE 5

Indole-carbamates synthesised in accordance with General Method C

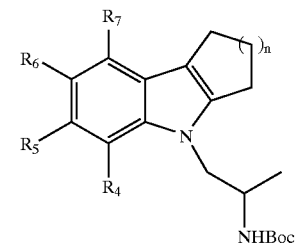

In this structural formula, there may be an additional double bond in the 5- or 6-membered ring fused to the indole ring. In Table 5 below, the substituents $R_4$ to $R_7$ are hydrogen unless otherwise stated (see column 2). In Table 5 below, the stereochemistry at the side chain is indicated in column 3.

| Compound | Substitution pattern | n | Yield | Data |
|---|---|---|---|---|
| 2c | $R_6 = F$ | 1 (S) | 79% | m.p. 169–170° C. (cyclohexane, 2-propanol); Found: C, 68.61; H, 7.68; N, 8.39%. $C_{19}H_{25}FN_2O_2$ requires: C, 68.65; H, 7.58; N, 8.42%. |
| 3c | $R_5 = Cl$ | 2 (S) | 83% | m.p. 165–166° C. (ethanol); Found: C, 66.16; H, 7.53; N, 7.72%. $C_{20}H_{27}ClN_2O_2$ requires: C, 66.19; H, 7.50; N, 7.72%. |
| 4c | $R_7 = Cl$ | 1 (S) | 78% | NMR (400 MHz, $CDCl_3$) $\delta_H$ 7.22(1H, m), 7.01 (1H, dd, J, 1.5, 8 Hz), 6.98(1H, t, J 8 Hz), 4.39 (1H, m, NH), 4.16(1H, m), 4.03(1H, sept., J 7 Hz), 3.92(1H, q, J 7 Hz), 3.06(2H, t, J 7 Hz), 2.85(2H, t, J 7 Hz), 2.52(2H, quint, J 7 Hz), 1.42 |

| Compound | Substitution pattern | n | Yield | Data |
|---|---|---|---|---|
| | | | | (9H, s), 1.10(3H, d, J 7 Hz); HPLC [Xterra, 2.0 mL/min; methanol-10 mM aqueous ammonium acetate solution (50:50) to (80:20) over 4 min then (80:20)] 94% (7.87 min). |
| 5c | $R_5$ = Cl | 1 (S) | 94% | m.p. 172–174° C.; NMR (400 MHz, CDCl$_3$) δ$_H$ 7.29(1H, m) 7.29(1H, d, J 8 Hz), 7.01(1H, dd, J 1.5, 8 Hz), 4.42(1H, m, NH), 4.12–3.89(3H, m), 2.85(2H, t., J 7 Hz), 2.81(2H, t, J 7 Hz), 2.52 (2H, quint., J 7 Hz), 1.42(9H, s), 1.11(3H, d, J 6.5 Hz). |
| 6c | $R_5$ = Cl; n in the above formula is not applicable; the compound contains an S-heteroatom: <br><br> Stereochemistry is (S) | | — | Not isolated, material deprotected in situ with excess potassium hydroxide. |
| 7c | $R_5$ = Br | 1 (S) | 43% | NMR (400 MHz, CDCl$_3$) δ$_H$ 7.44(1H, m), 7.25 (1H, d, J 8 Hz), 7.15(1H, dd, J 8, 1.5 Hz), 4.42 (1H, m, NH), 4.14–3.90(3H, m), 2.83(4H, obs. quint., J 7 Hz), 2.52(2H, quint., J 7 Hz), 1.43(9H, s), 1.12(3H, d, J 7 Hz); HPLC: [Supelcosil ABZ+ 1.0 ml/min, methanol-10 mM aqueous ammonium acetate solution(80:20)] 99% (8.07 (min). |
| 8c | $R_5$ = Br | 2 (S) | 24% | NMR (400 MHz, CDCl$_3$) δ$_H$ 7.45(1H, m), 7.29 (1H, d, J 8 Hz), 7.14(1H, dd, J 8, 1.5 Hz), 4.42 (1H, m, NH), 4.11(1H, m), 4.02(1H, obs. sept., J 7 Hz), 3.87(1H, q, J 7 Hz), 2.68(4H, q, J 6 Hz), 1.96–1.88(2H, m), 1.88–1.80(2H, m), 1.40(9H, s), 1.10(3H, d, J 6.5 Hz); HPLC: [Supelcosil ABZ+ 1.0 ml/min, methanol-10 mM aqueous ammonium acetate solution (80:20)] 97% (10.12 min). |
| 9c | $R_6$ = Cl | 2 (S) | 30% | NMR (400 MHz, CDCl$_3$) δ$_H$ 7.40(1H, d, J 2 Hz), 7.29(1H, m), 7.07(1H, dd, J 8.5, 2 Hz), 4.42(1H, m, NH), 4.18(1H, m), 4.02(1H, dq, J 20, 7 Hz), 3.85(dd, J 14.5, 7.5 Hz), 2.72(2H, obs. t, J 6 Hz), 2.66(2H, obs. t, J 6 Hz), 1.96–1.89(2H, m), 1.88–1.81(2H, m), 1.42(9H, s), 1.08(3H, d, J 6.5 Hz); HPLC: [Supelcosil ABZ+ 1.0 ml/min, methanol-10 mM aqueous ammonium acetate solution (50:50)] 96% (9.58 min). |
| 10c | $R_6$ = Cl | 1 (S) | 29% | NMR (400 MHz, CDCl$_3$) δ$_H$ 7.37(1H, br. d, J 2 Hz), 7.26(1H, m), 7.04(1H, dd, J 8.5, 2 Hz), 4.41 (1H, m, NH), 4.16(1H, m), 4.03(1H, m), 3.92 (1H, q, J 7 Hz), 2.86(2H, t, J 7 Hz), 2.81(2H, t, J 7 Hz), 2.52(2H, quint., J 7 Hz), 1.44(9H, s), 1.09 (3H, d, J 6.5 Hz); HPLC: [Supelcosil ABZ+ 1.0 ml/min, methanol-10 mM aqueous ammonium acetate solution (80:20)] 97% (7.82 min). |
| 11c | $R_5$ = OMe | 1 (S) | 64% | NMR (400 MHz, CDCl$_3$) δ$_H$ 7.28(1H, d, J 8.5 Hz), 6.94(1H, m), 6.73(1H, dd, J 2.5, 8.5 Hz), 4.48(1H, m, NH), 4.12(1H, m), 4.05(1H, m), 3.88(1H, dd, J 6.5, 14 Hz), 3.87(3H, s), 2.86–2.78 (4H, m), 2.55–2.46(2H, m), 1.43(9H, s), 1.11 (3H, d, J 7 Hz); HPLC: [Supelcosil ABZ+; 1.0 mL/min, methanol-10 mM aqueous ammonium acetate solution (80:20)] 96% (3.87 min). |
| 12c | $R_7$ = OMe | 1 (S) | 95% | NMR (400 MHz, CDCl$_3$) δ$_H$ 7.01(1H, t, J 7.5 Hz), 6.98(1H, m), 6.48(1H, dd, J 7, 1 Hz), 4.44 (1H, m, NH), 4.14(1H, m), 4.04(1H, m), 3.91 (1H, m), 3.90(3H, s), 2.97(2H, t, J 7 Hz), 2.82 (2H, t, J 7 Hz), 2.49(2H, quint., J 7 Hz), 1.44 (9H, s), 1.09(3H, d, J 6.5 Hz); HPLC: [Supelcosil |

-continued

| Compound | Substitution pattern | n | Yield | Data |
|---|---|---|---|---|
| | | | | ABZ+; 1.0 mL/min, methanol-10 mM aqueous ammonium acetate solution (80:20)] 90% (4.44 min). |
| 13c | $R_4 = R_5 = Cl$ | 1 (S) | 87% | m.p. 205–206° C. (cyclohexane, toluene); Found: C, 59.72; H, 6.34; N, 7.29; Cl, 18.77%. $C_{19}H_{24}Cl_2N_2O_2$ requires: C, 59.54; H, 6.31; N, 7.30; Cl, 18.50%. |
| 14c | | 1 (S) | 51% | m.p. 172–173° C.(isopropyl ether); Found: C, 71.46; H, 8.22; N, 8.78%. $C_{19}H_{26}N_2O_2.0.25H_2O$ requires: C, 71.55; H, 8.38; N, 8.78%. |
| 15c | $R_5 = R_7 = Cl$; n in the above formula is not applicable; the compound contains an S-heteroatom | | 82% | m.p. 201° C.(hexane); Found: C, 53.53; H, 4.99; N, 6.90%. $C_{18}H_{20}Cl_2N_2O_2S.0.25H_2O$ requires: C, 53.60; H, 5.12; N, 6.95%. |

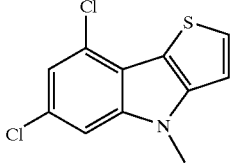

Stereochemistry is (S)

| Compound | Substitution pattern | n | Yield | Data |
|---|---|---|---|---|
| 16c | $R_5 = Cl$<br>$R_6 = F$ | 1 (S) | 74% | m.p. 173.5–176° C. (hexane); Found: C, 61.45; H, 6.54; N, 7.49%. $C_{19}H_{24}ClFN_2O_2.0.25H_2O$ requires: C, 61.45; H, 6.65; N, 7.54%. |
| 17c | $R_5 = CF_3$ | 1 (S) | 76% | 147–151° C. (hexane); Found: C, 62.22; H, 6.70; N, 7.24%. $C_{20}H_{25}F_3N_2O_2.025H_2O$ requires: C, 62.08; H, 6.64; N, 7.24%. |
| 18c | $R_7 = Cl$<br>$R_6 = F$ | 1 (S) | 88% | m.p. 161–162° C. (2-propanol); NMR (400 MHz, CDCl$_3$) $\delta_H$ 7.17(1H, m), 6.58(1H, t, J 9 Hz), 4.40 (1H, m), 4.17(1H, m), 4.01(1H, dt, J 7, 12.5 Hz), 3.89(1H, q, J 7 Hz), 3.05(2H, t, J 7 Hz), 2.84 (2H, t, J 7 Hz), 2.52(2H, quintet, J 7 Hz), 1.42 (9H, s) and 1.10(3H, d, J 6.5 Hz). |
| 19c | $R_5 = R_6 = Cl$ | 1 (S) | 81% | m.p. 183–184° C. (hexane); Found: C, 59.45, H, 6.29; N, 7.25%. $C_{19}H_{24}Cl_2N_2O_2$ requires: C, 59.54; H, 6.31; N, 7.30%. |
| 20c | $R_6 = OMe$ | 1 (S) | 63% | m.p. 121° C.; Found: C, 69.66; H, 8.36; N, 7.94%. $C_{20}H_{28}N_2O_3$ requires: C, 69.74; H, 8.19; N, 8.13%. |
| 21c | $R_7 = CF_3$ | 1 (S) | 62% | m.p. 154–155° C. (hexane); Found: C, 61.71; H, 6.60; N, 7.13%. $C_{20}H_{25}F_3N_2O_2.05H_2O$ requires: C, 61.37; H, 6.70; N, 7.16%. |
| 22c | $R_6 = R_7 = Cl$ | 1 (S) | 65% | m.p. 152–154° C. (hexane); Found: C, 59.01; H, 6.27; N, 7.08%. $C_{19}H_{24}Cl_2N_2O_2.0.25H_2O$ requires: C, 58.84; H, 6.37; N, 7.22%. |
| 23c | $R_7 = OBn$ | 1 (S) | | NMR (400 MHz, CDCl$_3$) $\delta_H$ 7.49(2H, d, J 7 Hz), 7.38(2H, t, J 7 Hz), 7.30(1H, t, J 7 Hz), 6.99(2H, m), 6.55(1H, m), 5.18(2H, s), 4.44(1H, m, NH), 4.15(1H, m), 4.05(1H, obs. septet, J 6.5 Hz), 3.92(1H, q, J 7 Hz), 3.02(2H, t, J 7 Hz), 2.84 (2H, t, J 7 Hz), 2.51(2H, quint., J 7 Hz), 1.44 (9H, s), 1.10(3H, d, J 7 Hz); HPLC: [Supelcosil ABZ+; 1.0 mL/min, methanol-10 mM aqueous ammonium acetate solution (80:20)] 97% (9.80 min). |
| 24c | $R_7 = O^iPr$ | 1 (S) | 4% | Used immediately without purification or characterisation. |
| 25c | $R_5 = O^iPr$ | 1 (S) | 2% | Used immediately without purification or characterisation. |
| 26c | $R_5 = R_7 = Cl$ | 1 (S) | 75% | m.p. 166–166.5° C. (hexane); Found: 58.90; H, 6.22; N, 7.16%. $C_{19}H_{24}Cl_2N_2O_2.0.25H_2O$ requires: C, 58.84; H, 6.37; N, 7.22%. |
| 27c | $R_5 = EtS$ | 1 (S) | 33% | NMR (400 MHz, CDCl$_3$) $\delta_H$ 1.11(3H, d, J 6.02 Hz), 1.25(3H, t, J 6.53 Hz), 1.41(9H, br s), 2.5(2H, m), 2.77–2.94(6H, m), 3.91–4.16(3H, m), 7.12(1H, d, J 7.53 Hz), 7.32(1H, d, J 7.53), 7.4(1H, br s); HPLC: [Supelcosil ABZ+; 1.0 |

-continued

| Compound | Substitution pattern | n | Yield | Data |
|---|---|---|---|---|
| 28c | $R_4$ = $OCF_3$ | 1 (S) | 78% | ml/min, methanol-10 mM aqueous ammonium acetate solution (80:20)] 91% (7.61 min). NMR (400 MHz, CDCl$_3$) $\delta_H$ 7.28(1H, dd, J 6.2, 2.9 Hz), 6.96–6.95(2H, m), 4.39(1H, br s), 4.15 (2H, br s), 4.00(1H, br d, J 6.4 Hz), 2.87(2H, br s), 2.79(2H, obs t, J 7.2 Hz), 2.50(2H, obs t, J 6.7 Hz), 1.32(9H, br s), 1.13(3H, br d, J 6.4 Hz); HPLC: [Supelcosil ABZ+; 1.0 ml/min, methanol-10 mM aqueous ammonium acetate solution (80:20)] 94% (8.79 min). |
| 29c | $R_6$ = $OCF_3$ | 1 (S) | 30% | m.p. 123° C.; NMR (400 MHz, CDCl$_3$) $\delta_H$ 7.32 (1H, d, J 8 Hz), 7.25(1H, d), 6.96(1H, dd, J 8, 2 Hz), 4.41(1H, m, NH), 4.18(1H, m), 4.04(1H, sept., J 7 Hz), 3.93(1H, q, J 7 Hz), 2.90–2.80(4H, m), 2.53(2H, quint, J 7 Hz), 1.42(9H, s), 1.12 (3H, d, J 6.5 Hz), HPLC: [Supelcosil ABZ+; 1.0 ml/min, methanol-10 mM aqueous ammonium acetate solution (80:20)] 96% (7.47 min). |
| 30c |  | 1 (R) | 74% | m.p. 170–172° C. (hexane); Found: C, 71.08; H, 8.27; N, 8.71%. $C_{19}H_{26}N_2O_2 \cdot 0.67H_2O$ requires: C, 71.22; H, 8.39; N, 8.74%. |
| 31c | $R_5$ = F | 1 (S) | 59% | m.p. 167–174° C. (hexane); Found: C, 65.76; H, 7.30; N, 7.98%. $C_{19}H_{25}FN_2O_2 \cdot 0.75H_2O$ requires: C, 65.97; H, 7.72; N, 8.10%. |
| 32c | n in the above formula is not applicable; the compound contains an S-heteroatom: 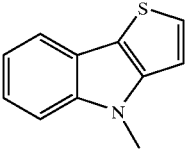 Stereochemistry is (S) |  | 21% | (aromatisation during reaction and work-up) m.p. 200° C. (hexane); Found: C, 65.08; H, 6.65; N, 8.39%. $C_{18}H_{22}N_2O_2S$ requires: C, 65.43; H, 6.71; N, 8.47%. |
| 33c | $R_5$ = $R_6$ = F | 1 (S) | 43% | Mixture of inseparable regioisomers (with 7,8-difluoro). |
| 34c | $R_7$ = Cl $R_6$ = Me | 1 (S) | 70% | NMR (400 MHz, CDCl$_3$) $\delta_H$ 7.12(1H, d, J 8 Hz), 6.92(1H, d, J 8 Hz), 4.40(1H, m, NH), 4.14(1H, m), 4.02(1H, dt, J 6.5, 12 Hz), 3.90(1H, q, J 7 Hz), 3.06(2H, t, J 7 Hz), 2.83(2H, t, J 7 Hz), 2.50 (2H, quintet, J 7 Hz), 2.42(3H, s), 1.43(9H, s) and 1.08(3H, d, J 6.5 Hz); HPLC: [Supelcosil ABZ+; 1.0 mL/min, methanol-10 mM aqueous ammonium acetate solution (80:20)] 98% (8.70 min). |
| 35c | $R_7$ = Cl $R_6$ = Me | 1 (R) | 92% | NMR (400 MHz, CDCl$_3$) $\delta_H$ 7.12(1H, d, J 8 Hz), 6.91(1H, d, J 8 Hz), 4.41(1H, m, NH), 4.12(1H, m), 4.02(1H, m), 3.98(1H, q, J 7 Hz), 3.06(2H, t, J 7 Hz), 2.82(2H, t, J 7 Hz), 2.50(2H, quintet, J 7 Hz), 2.42(3H, s), 1.43(9H, s) and 1.08(3H, d, J 6.5 Hz); HPLC: [Supelcosil ABZ+; 1.0 ml/min, methanol-10 mM aqueous ammonium acetate solution (80:20)] 98% (8.62 min). |
| 36c | $R_6$ = F $R_5$ = OMe | 1 (R) | 40% | Crystallised from Ethanol/water (5:1); NMR (400 MHz, CDCl$_3$) $\delta_H$ 7.05(2H, d, J 12.2 Hz), 4.48–4.34(1H, m), 4.2–3.98(2H, m), 3.92(3H, s, MeO), 3.84(1H, dd, J 14.0, 7.1 Hz), 2.80(2H, t, J 7.0 Hz), 2.76(2H, t, J 7.2 Hz), 2.48(2H, m), 1.40 (9H, br s), 1.09(3H, d, J 6.5 Hz); ). HPLC: [Supelcosil AHZ+; 1.0 ml/min, methanol-10 mM aqueous ammonium acetate solution (70:30)] 99% (8.82 min) and [Xterra; 2.0 mL/min, methanol-10 mM aqueous ammonium acetate solution, gradient elution 50% to 80% methanol over the first 4 min, then 80:20] 96% (6.89 min). |
| 37c | $R_6$ = F $R_5$ = OMe | 1 (S) | 36% | NMR (400 MHz, CDCl$_3$) $\delta_H$ 7.08(1H, br. s), 7.07 (1H, d, J 12 Hz), 4.41(1H, m, NH), 4.16(1H, m), 4.12(1H, m), 3.94(3H, s), 4.04(1H, dt, J 6.5, 12 Hz), 3.84(1H, q, J 7 Hz), 2.80(4H, m), 2.50(2H, |

-continued

| Compound | Substitution pattern | n | Yield | Data |
|---|---|---|---|---|
| | | | | quintet, J 7 Hz), 1.42(9H, s), 1.11(3H, d, J 6.5 Hz); HPLC: [Xterra; 2.0 ml/min, gradient elution, methanol-10 mM aqueous ammonium acetate solution (50:50) to (80:20) over 4 min then (80:20)] 97% (6.33 min). |
| 39c | $R_5 = R_6 = F$ | 1 (R) | 58% | m.p. 176–176.5° C. (hexane); Found: C, 61.71; H, 6.59; N, 7.49%. $C_{19}H_{24}ClFN_2O_2.0.25H_2O$ requires: C, 61.45; H, 6.65; N, 7.54%. |
| 40c | $R_7 = Cl$<br>$R_6 = F$ | 1 (R) | 64% | m.p. 160–161° C. (hexane); Found: C, 62.00; H, 6.61; N, 7.56%. $C_{19}H_{24}ClFN_2O_2$ requires: C, 62.21; H, 6.59; N, 7.63%. |
| 41c | $R_7 = Br$ | 1 (S) | 29% | m.p. 178° C. (2-propanol); Found: C, 58.02; H, 6.45; N, 7.09%. $C_{19}H_{25}BrN_2O_2$ requires: C, 58.02; H, 6.41; N, 7.12%. |
| 42c | $R_6 = F$<br>$R_7 = OMe$ | 1 (S) | 69% | NMR (400 MHz, $CDCl_3$) $\delta_H$ 6.99–6.94 (1H, m), 6.84(1H, dd, J 11.3, 9.4 Hz), 4.44–4.37(1H, m, NH), 4.16–4.00(2H, m), 4.00(3H, s), 3.87(1H, dd, J 14.0, 7.2 Hz), 2.96(2H, obs t, J 6.6 Hz), 2.83 (2H, obs t, J 7.3 Hz), 2.51(2H, quintet, J 7.0 Hz), 1.42(9H, br s), 1.11(3H, d, J 6.8 Hz); HPLC: [Xterra; 2.0 mL/min, methanol-10 mM aqueous ammonium acetate solution, gradient elution 50% to 80% over the first 4 min, then 80:20] 99.7% (6.55 min). |
| 43c | $R_4 = Cl$ | 1 (R) | 31% | m.p. 193–194° C.; Found: C, 65.27; H, 7.24; N, 7.96%. $C_{19}H_{25}ClN_2O_2$ requires: C, 65.41; H, 7.22; N, 8.03%. |
| 44c | $R_4 = Cl$ | 1 (S) | 25% | m.p. 192–193° C.; NMR (400 MHz, $CDCl_3$) $\delta_H$ 7.27(1H, dd, J 1, 8 Hz), 7.04(1H, dd, J 1, 8 Hz), 6.93(1H, t, J 8 Hz), 4.80–4.40(3H, m), 4.20–4.00 (2H, m), 2.89(2H, m), 2.81(2H, t, J 7 Hz), 2.51 (2H, quint., J 7 Hz), 1.28(9H, s), 1.17(3H, d, J 6.5 Hz). |

Compound 45c: (S) 4-[2tert-Butoxy-carbonylamio)propyl]-1-oxo-1,2,3,4-tetrabydrocyclopent[b]indole To a solution of TEMPO.tetrafluoroborate (2.8g, 11.5mmol) in acetonitrilelwater (9:1, 50 mL) was added dropwise a solution of (S) 4-[2tert-butoxyarbonylznio)propyl]-1,2,3,4-tetrahydrocyclopent[b]indole (1.5 g, 5.1 mmol) in acetonitrile—water (9:1, 50 mL). The mire was stirred for 16 h., then the solvent was removed in vacuo and the residue adsorbed onto alumina (20 g) and purified by column chromatography [$Al_2O_3$; heptane—ethyl acetate (10:3)] to afford the product (0.7 g, 42%) as a white solid; NMR (400 MHz, DMSO-$d_6$) $\delta_H$ 1.13 (3H, d, J 6.53Hz), 1.21 (9H, br s), 2.82 (2H, m), 3.09 (2H, m), 3.83–4.28 (3H, m), 6.94 (1H, d, J 8.03Hz), 7.19 (1H, t, J 7.53Hz), 7.27 (1H, d t, J 1.0 Hz, 7.53 Hz), 7.58–7.71 (2H, m); IR $\nu_{max}$ (nujol)/cm$^{-1}$ 3365, 2924, 2854, 1685, 1538, 1524, 1478, 1452, 1366, 1248, 1168, 1052 and743.

Deprotection of the Amine (General Method D)

The protected amines prepared as described above were deprotected in accordance with the following synthetic methods (General Methods D(i), D(ii) and D(iii)) given below for Examples 23, 36 and 45, to give compounds of formula (I). Data for these Examples are given in Table 6.

Method D(i): Deprotection using Hydrogen Chloride

Example 23

(S)-1-(8-Benzyloxy-1,2,3,4-tetrahydrocyclopent[b]indolyl)-2-propylamine, hydrochloride To a stirred solution of (S) 8-benzyloxy4-[2-tert-butoxy-carbonylamino)propyl]-1,2,3,4-tetrahydrocyclopent[b]indole (250 mg, 0.59 mmol) in methanol (10 mL) under an atmosphere of Ar at ambient temperature was added hydrogen chloride (4 M in dioxane; 1.4 mL, 5.6 mmol) and then the mixture was stirred for 16 h. Ether (20 mL) was added, and the resultant suspension was cooled (ice-water bath), filtered, and the solid washed with ice-cold ether to afford the product (183 mg, 89%) as a pale turquoise powder. Data for (S)-1-(8-benzyloxy-1,2,3,4-tetrahydrocyclopent[b]indol-4-yl)-2-propylamine, hydrochloride are included below in Table 6.

Method D(u): Deprotection using Potassium tert-Butoxide

Example 36

(R)-1-(7-Fluoro-1,2,3,4-tetrahydro-6-methoxy-cyclopent[b]indol-4-yl)-2-propylamine, hemifumarate To a stirred solution of (R) 4-[2-(tert-butoxy-carbonylamino)propyl]-7-fluoro-1,2,3,4-tetrahydro-6methoxy-cyclopent[b]indole (0.405 g, 1.12 mmol) in methyl sulfoxide (10 mL), under argon at 0° C. was added potassium tert-butoxide (0–126 g, 1.12 mmol) portionwise over 4 min. The reaction was stirred under argon at room temperature for 20 h poured into ice/water (2:1, 150 mL) and stirred until all the ice had melted. The aqueous suspension was extracted with ethyl acetate (2×50 mL). The combined organic extracts were successively washed with water (2×20 mL), brine (20 mL) then dried ($NgSO_4$), filtered and concentrated in vacuo. The residue was dissolved in hot 2-propanol (5 mL) and added dropwise to a stirred solution of fumaric acid (0.12 g, 1 mmol) in hot 2-propanol (5 nL). The mixture was cooled to 0° C., diluted with ether (50 mL) and filtered. The filter-cake was washed (icecold 2-propanol, ether) and dried in vacuo to yield the hemifumarate as an off-white solid (0.27 g, 75%). Data for (R)-1-(7-fluoro-1,2,3,4-tetrahydro-6-methoxy-cyclopent[b]indol-4-yl)-2-propylamine, hemifumarate are included in Table 6 below.

Method D(iii): Deprotection using Trifluoroacetic Acid

Example 45

(S)-1-(3,4Dihydro-1-oxo-2H-hydrocyclopent[b]indol-4-yl)-2-propylamine hydrochloride A stirred solution of (S) 4-[2-tert-butoxy-carbonylamino)propyl]-3,4-dihydro-1-oxo-2H-cyclopent[b]indole (0.1 g, 0.3 mmol) in dichloromethane (5 mL) was cooled to 0° C. (ice). Trifluoroacetic acid (2 mL, 26 mmol) was added dropwise to the mixture and stirring was continued at 0° C. for 5 h The mixture was poured onto ice-water (10 mL). basified (pH 8–9) using aqueous sodium hydroxide solution (2 N) then extracted with dichloromethane (2×10 mL). The organic extracts were combined, dried ($MgSO_4$), evaporated to dryness then dissolved in methanol-dichloromethane (1:9, 10 mL), treated with ethereal hydrogen chloride solution (1 M, 1 mmol) and concentrated in vacuo to give the title compound as a white solid (0.057 g, 72%). Data for Example 45 are listed below in Table 6.

TABLE 6

Indole-propylamines of formula (I) synthesised using General Method D

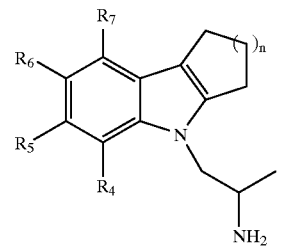

In this structural formula, there may be an additional double bond in the 5- or 6-membered ring fused to the indole ring. In Table 6 below, the substituents $R_4$ to $R_7$ are hydrogen unless otherwise stated (see column 2). In Table 6 below, the stereochemistry at the side chain is indicated in column 3.

| Example | Substitution pattern | n | Yield (method) | Data |
|---|---|---|---|---|
| 2 | $R_6$ = F (S) | 1 | 63% (i) | Fumarate. m.p. 161–162° C.; Found: C, 61.33; H, 6.11; N, 8.05%. $C_{18}H_{21}FN_2O_4 \cdot 0.25H_2O$ requires: C, 61.27; H, 6.14; N, 7.94%. |
| 3 | $R_5$ = Cl (S) | 2 | 84% (i) | Fumarate. m.p. 205° C. (dec.); Found: C, 59.50; H, 6.13; N, 7.23%. $C_{19}H_{23}ClN_2O_4 \cdot 0.25H_2O$ requires: C, 59.53; H, 6.18; N, 7.31%. |
| 4 | $R_7$ = Cl (S) | 1 | 25% (i) | Fumarate. m.p. 172–173° C. (dec.); Found: C, 58.63; H, 5.69; N, 7.44%. $C_{14}H_{17}ClN_2 \cdot 1.1 C_4H_4O_4$ requires: C, 58.71; H, 5.73; N, 7.44%. |
| 5 | $R_5$ = Cl (S) | 1 | 17% (ii) | Fumarate. m.p. 175–180° C. (dec.); Found: C, 59.01; H, 5.91; N, 7.34%. $C_{18}H_{21}ClN_2O_4$ requires: C, 59.26; H, 5.80; N, 7.67%. |
| 6 | $R_5$ = Cl; n in the above formula is not applicable; the compound contains an S-heteroatom: 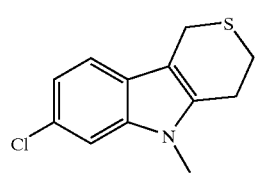 Stereochemistry is (S) | | 2% (ii) | Hemifumarate. m.p. 189–192° C.; NMR (400 MHz, DMSO-$d_6$) $\delta_H$ 7.64(1H, d, J 2 Hz), 7.45 (1H, d, J 8.5 Hz), 7.04(1H, dd, J 2, 8.5 Hz), 6.47 (1H, s), 4.11(1H, q, J 7 Hz), 4.04(1H, q, J 7 Hz), 3.81(2H, s), 3.36(2H, m), 3.08–2.91(4H, m), 1.04(3H, d, J 6.5 Hz). |
| 7 | $R_5$ = Br (S) | 1 | 35% (i) | Hemifumarate. NMR (400 MHz, DMSO-$d_6$) $\delta_H$ 7.71(1H, d, J 2 Hz), 7.30(1H, d, J 8.5 Hz), 7.11 (1H, dd, J 8.5, 2 Hz), 6.46(1H, s), 4.08(1H, dd, J 14.5, 6.5 Hz), 3.98(dd, J 14.5, 7 Hz), 3.35(4H, m,), 2.86(2H, m), 2.76(2H, m), 2.48(2H, quint., J 7 Hz), 1.05(3H, d, J 6.5 Hz); HPLC: [Supelcosil ABZ+ 1.0 ml/min, methanol-10 mM aqueous ammonium acetate solution (80:20)] 97% (4.38 min). |
| 8 | $R_5$ = Br (S) | 2 | 51% (i) | Hemifumarate. NMR (400 NHz, DMSO-$d_6$) $\delta_H$ 7.73(1H, d, J 1.5 Hz), 7.34(1H, d, J 8.5 Hz), 7.12 (1H, dd, J 8.5, 1.5 Hz), 6.48(1H, s), 4.13(1H, dd, J 14.5, 6.5 Hz), 4.04(1H, dd, J 14.5, 7.5 Hz), 3.41 (1H, obs. sextet, J 7 Hz), 2.80–2.68(2H, m), 2.63 (2H, m), 1.82(2H, m), 1.79(2H, m), 1.06(3H, d, J 6.5 Hz); HPLC: [Supelcosil ABZ+ 1.0 ml/min, methanol-10 mM aqueous ammonium acetate solution (80:20)] 97% (5.17 min). |

-continued

| Example | Substitution pattern | n | Yield (method) | Data |
|---|---|---|---|---|
| 9 | $R_6$ = Cl | 2 (S) | 78% (i) | Fumarate. NMR (400 MHz, DMSO-$d_6$) $\delta_H$ 7.49 (1H, d, J 8.5 Hz), 7.42(1H, d, J 2 Hz), 7.08(1H, dd, J 8.5, 2 Hz), 6.50(2H, s), 4.23(1H, dd, J 14.5, 6.5 Hz), 4.11(1H, dd, J 14.5, 8.5 Hz), 3.47(1H, obs. sextet, J 7 Hz), 2.81–2.66(2H, m), 2.65–2.59 (1H, m), 1.91–1.83(2H, m), 1.83–1.74(2H, m), 1.07(3H, d, J 6.5 Hz); HPLC: [Supelcosil ABZ+ 1.0 ml/min, methanol-10 mM aqueous ammonium acetate solution (80:20)] 97% (5.10 min). |
| 10 | $R_6$ = Cl | 1 (S) | 62% (i) | Fumarate. NMR (400 MHz, DMSO-$d_6$) $\delta_H$ 7.49 (1H, d, J 8.5 Hz), 7.39(1H, d, J 2 Hz), 7.06(1H, dd, J 8.5, 2 Hz), 6.50(2H, s), 4.25(1H, dd, J 14.5, 6.5 Hz), 4.09(1H, dd, J 14.5, 8 Hz), 3.47(1H, obs. sextet, J 7 Hz), 2.92(1H, dd, J 15.5, 7 Hz), 2.84(1H, dd, J 15.5, 7.5 Hz), 2.76(2H, t, J 7 Hz), 2.47(2H, quint, J 7 Hz), 1.09(3H, d, J 6.5 Hz); HPLC: [Supelcosil ABZ+ 1.0 ml/min, methanol-10 mM aqueous ammonium acetate solution (80:20)] 97% (4.48 min). |
| 11 | $R_5$ = OMe | 1 (S) | 73% (i) | Fumarate. m.p. 182° C.; Found: C, 63.37; H, 6.75; N, 7.76%. $C_{19}H_{24}N_2O_5$ requires: C, 63.32; H, 6.71; N, 7.77%. |
| 12 | $R_7$ = OMe | 1 (S) | 75% (i) | Fumarate. NMR(400 MHz, DMSO-$d_6$) $\delta_H$ 7.05 (1H, d, J 8 Hz), 6.96(1H, t, J 8 Hz), 6.51(1H, d, J 8 Hz), 6.50(2H, s), 4.24(1H, dd, J 14.5, 6 Hz), 4.04(1H, 14.5, 8 Hz), 3.82(3H, s), 3.47(1H, sextet, J 7 Hz), 2.90–2.75(4H, m), 2.45(2H, quint., J 7 Hz), 1.08(3H, d, J 6.5 Hz), HPLC: [Supelcosil ABZ+ 1.0 ml/min, methanol-10 mM aqueous ammonium acetate solution (80:20)] 96% (2.90 min). |
| 13 | $R_4$ = $R_5$ = Cl | 1 (S) | 84% (i) | Hydrochloride. m.p. 288–291° C.; Found: C, 52.84; H, 5.38; N, 8.76; Cl, 33.48%. $C_{14}H_{17}Cl_3N_2$ requires: C, 52.60; H, 5.36; N, 8.76; Cl, 33.27%. |
| 14 | | 1 (S) | 90% (i) | Hydrochloride. m.p. 233° C. (ethyl acetate); Found: 65.29; H, 7.52; N, 10.81%. $C_{14}H_{18}N_2$.Hydrochloride.0.375$H_2O$ requires: C, 65.30; H, 7.73; N, 10.88%. |
| 15 | $R_5$ = $R_7$ = Cl; n in the above formula is not applicable; the compound contains an S-heteroatam | | 74% (i) | Hydrochloride. m.p. 316–322° C. (ethyl acetate); Found: C, 44.54; H, 3.78; N, 7.84%. $C_{13}H_{12}Cl_2N_2S$.Hydrochloride.$H_2O$ requires: C, 44.15; H, 4.27; N, 7.92%. |

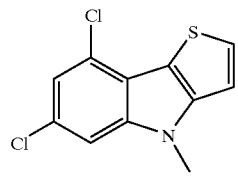

Stereochemistry is (S)

| | | | | |
|---|---|---|---|---|
| 16 | $R_5$ = Cl $R_6$ = F | 1 (S) | 15% (iii) | NMR (400 MHz, DMSO-$d_6$) $\delta_H$ 1.18(3H, d, J 6.53 Hz), 2.46(2H, m), 2.73(2H, m), 2.78–2.95 (2H, m), 3.57(1H, m), 4.15(1H, dd, J 7.53 Hz, 14.56 Hz), 4.36(1H, dd, J 6.53 Hz, 14.05 Hz), 7.33 (1H, d, J 9.54 Hz), 7.80(1H, d, J 6.53 Hz), 8.27 (3H, br s); HPLC: [Supelcosil ABZ+; 1.0 ml/min, methanol-10 mM aqueous ammonium acetate solution (80:20)] 96% (4.28 min). |
| 17 | $R_5$ = $CF_3$ | 1 (S) | 94% (i) | Hydrochloride. m.p. 270–274° C. (ethyl acetate); Found: C, 56.31; H, 5.83; N, 8.66%. $C_{15}H_{17}F_3N_2$.HCl requires: C, 56.52; H, 5.69; N, 8.78%. |
| 18 | $R_7$ = Cl $R_6$ = F | 1 (S) | 25% (i) | Hydrochloride. m.p. 252–253° C. (ether); Found: C, 54.12; H, 5.60; N, 8.91%. $C_{14}H_{17}Cl_2FN_2$.0.5$H_2O$ requires: C, 53.86; H, 5.81; N, 8.97%. |
| 19 | $R_5$ = $R_6$ = Cl | 1 (S) | 93% (i) | Hydrochloride. m.p. 292–295° C. (ethyl acetate); Found: C, 52.20; H, 5.29; N, 8.63%. |

-continued

| Example | Substitution pattern | n | Yield (method) | Data |
|---|---|---|---|---|
| | | | | $C_{14}H_{16}Cl_2N_2 \cdot HCl \cdot 0.25H_2O$ requires: C, 51.87; N, 5.44; N, 8.64%. |
| 20 | $R_6$ = OMe | 1 (S) | 79% (i) | Hydrochloride. m.p. 260° C. (dec.); NMR (400 MHz, DMSO-$d_6$) $\delta_H$ 8.37(3H, m, NH$_3$), 7.40(1H, d, J 8.5 Hz), 6.88(1H, d, J 2.5 Hz), 6.71(1H, dd, J 8.5, 2.5 Hz), 4.36(1H, dd, J 14.5, 6 Hz), 4.11 (1H, dd, J 14.5, 8 Hz), 3.76(3H, s), 3.54(1H, m), 3.39(1H, m), 2.94–2.78(2H, m), 2.75(2H, t, J 7 Hz), 2.47(2H, quintet, J 7 Hz), 1.16(3H, d, J 6.5 Hz). |
| 21 | $R_7$ = CF$_3$ | 1 (S) | 59% (i) | Hydrochloride. m.p. 238–242° C.; NMR (400 MHz, DMSO-$d_6$) $\delta_H$ 8.40(3H, m, NH$_3$), 7.89(1H, d, J 8 Hz), 7.39(1H, d, J 8 Hz), 7.23 (1H, t, J 7 Hz), 4.47(1H, dd, J 14.5, 6.5 Hz), 4.28(1H, dd, J 14.5, 7.5 Hz), 3.61(1H, m), 3.39(1H, m), 3.04–2.86(2H, m), 2.82(2H, t, J 7 Hz), 2.50(2H, quint., J 7 Hz), 1.22(3H, d, J 6.5 Hz). |
| 22 | $R_6 = R_7$ = Cl | 1 (S) | 74% (i) | Hydrochloride. m.p. 243–248° C. (ethyl acetate); Found: C, 51.20; H, 5.30; N, 8.28%. $C_{14}H_{16}Cl_2N_2 \cdot HCl \cdot 0.5H_2O$ requires: C, 51.16; H, 5.52; N, 8.52%. |
| 23 | $R_7$ = OBn | 1 (S) | 86% | Hydrochloride. NMR (400 MHz, DMSO-$d_6$) $\delta_H$ 8.35(3H, m, NH$_3$), 7.50(2H, d, J 7.5 Hz), 7.42 (2H, t, J 7.5 Hz), 7.33(1H, t, J 7.5 Hz), 7.12(1H, d, J 8.5 Hz), 6.98(1H, t, J 8 Hz), 6.63(1H, d, J 8 Hz), 5.19(2H, s), 4.36(1H, dd, J 14.5, 6 Hz), 4.13 (1H, dd, J 14.5, 8 Hz), 3.56(1H, m), 3.44(1H, m), 2.96–2.77(4H, m), 2.48(2H, quint., J 7 Hz), 1.17 (3H, d, J 6.5 Hz); HPLC: [Supelcosil ABZ+; 1.0 ml/min, methanol-10 mM aqueous ammonium acetate solution (80:20)] 97% (5.15 min). |
| 24 | $R_7$ = O$^i$Pr | 1 (S) | 43% (iii) | Fumarate. m.p. 189° C. (dec.); NMR (400 MHz, DMSO-$d_6$) $\delta_H$ 7.02(1H, d, J 8.0 Hz), 6.93(1H, t, J 7.4 Hz), 6.49(2H, s), 4.58(1H, quint, J 6.0 Hz), 4.17(1H, dd, J 14.4, 6.2 Hz), 4.00(1H, dd, J 14.4, 7.8 Hz), 3.44(1H, obs sextet, J 6.7 Hz), 2.91–2.76 (4H, m), 2.44(2H, obs quint, J 7.0 Hz), 1.30(6H, d, J 6.0 Hz), 1.08(3H, d, J 6.5 Hz); HPLC: [Supelcosil ABZ+; 1.0 ml/min, methanol-10 mM aqueous ammonium acetate solution (80:20)] 98.4% (3.33 min); Found C, 65.31; H, 7.36; N, 7.36%. $C_{21}H_{28}N_2O_5$ requires: C, 64.93; H, 7.26; N, 7.21% |
| 25 | $R_5$ = O$^i$Pr | 1 (S) | 35% (ii) | Hemifumarate. m.p. 163° C. (dec.); NMR (400 MHz, DMSO-$d_6$) $\delta_H$ 7.19(1H, d, J 8.6 Hz), 7.02 (1H, d, J 2.0 Hz), 6.61(1H, dd, J 8.6, 2.0 Hz), 6.46(1H, s), 4.61(1H, quint, J 6.0 Hz), 4.07(1H, dd, J 14.3, 6.2 Hz), 3.92(1H, dd, J 14.3, 7.5 Hz), 3.34(1H, q, J 6.7 Hz), 2.88–2.78(2H, m), 2.73 (2H, obs t, J 6.8 Hz), 2.45(2H, obs quint, J 6.9 Hz), 1.27(6H, d, J 6.0 Hz), 1.04(3H, d, J 6.7 Hz); HPLC: [Supelcosil ABZ+; 1.0 ml/min, methanol-10 mM aqueous ammonium acetate solution (80:20)] 97% (3.35 min); Found C, 69.04; H, 7.92; N, 8.42%. $C_{19}H_{26}N_2O_3$ requires: C, 69.07; H, 7.93; N, 8.47%. |
| 26 | $R_5 = R_7$ = Cl | 1 (S) | 99% (i) | Hydrochloride. m.p. 258° C. (ethyl acetate); Found: C, 52.02; H, 5.28; N, 8.53%. $C_{14}H_{16}Cl_2N_2 \cdot HCl \cdot 0.25H_2O$ requires: C, 51.87; H, 5.44; N, 8.64%. |
| 27 | $R_5$ = EtS | 1 (S) | 46% | Hydrochloride. m.p. 115–119° C.; NMR (400 MHz, DMSO-$d_6$) $\delta_H$ 1.17(6H, m), 2.46(2H, m), 2.73(2H, m), 2.85,(2H, m), 2.95(2H, q, J 7.53 Hz), 3.53(1H, m), 4.14(1H, dd, J 7.53, 14.05), 4.36(1H, dd, J 6.53 Hz, 14.05 Hz), 7.02 (1H, d, J 8.53 Hz), 7.29(1H, d, J 8.53 Hz), 7.56 (1H, br s), 8.34(3H, br s). |
| 28 | $R_4$ = OCF$_3$ | 1 (S) | 70% (i) | Hydrochloride. m.p. 281° C. (dec); NMR (400 MHz, DMSO-$d_6$) $\delta_H$ 8.45(3H, m, NH$_3$), 7.38(1H, dd, J 7.2, 1.5 Hz), 7.11–7.05(2H, m), 4.37(1H, dd, J 14.8, 7.1 Hz), 4.29(1H, dd, J 14.8, 6.9 Hz), 3.52(1H, q, J 6.5 Hz), 3.00(1H, obs quint, J 7.5 Hz), 2.89(1H, obs quint, J 6.9 Hz), 2.81–2.78(2H, m), 2.53–2.47(2H, m), 1.16(3H, d, J 6.7 Hz); HPLC: [Supelcosil ABZ+; 1.0 ml/min, methanol- |

-continued

| Example | Substitution pattern | n | Yield (method) | Data |
|---|---|---|---|---|
| | | | | 10 mM aqueous ammonium acetate solution (80:20)] 99.8% (3.80 min). |
| 29 | $R_6$ = $CF_3$ | 1 | 95% (i) | Hydrochloride. m.p. 166–169° C.; NMR (400 MHz, DMSO-$d_6$) $\delta_H$ 8.43(3H, m, $NH_3$), 7.66(1H, d, J 9 Hz), 7.33(1H, d, J 1.5 Hz), 7.05(1H, dd, J 9, 1.5 Hz), 4.44(1H, dd, J 14.5, 6.5 Hz), 4.21(1H, dd, J 14.5, 8 Hz), 3.59(1H, m), 3.00–2.81(2H, m), 2.78(2H, t, J 7 Hz), 2.49(2H, quint, J 7 Hz), 1.20 (3H, d, J 6.5 Hz). |
| 30 | | 1 (R) | 92% (i) | Hydrochloride. m.p. 225–231° C. (dec.); Found: C, 65.37; H, 7.51; N, 10.78%. $C_{14}H_{18}N_2 \cdot HCl \cdot 0.33H_2O$ requires: C, 65.49; H, 7.33; N, 10.91%. |
| 31 | $R_5$ = F | 1 (S) | 40% (i) | Hydrochloride. m.p. 215° C. (ether); Found: C, 60.38; H, 6.58; N, 9.85%. $C_{14}H_{17}FN_2 \cdot HCl \cdot 0.5H_2O$ requires: C, 60.54; H, 6.53; N, 10.09%. |
| 32 | n in the above formula is not applicable; the compound contains an S-heteroatom: 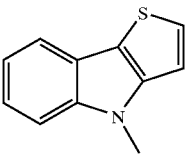 Stereochemistry is (S) | | 97% (i) | Hydrochloride. m.p. 289–293° C. (ethyl acetate); Found: C, 58.57; H, 5.77; N, 10.49%. $C_{13}H_{14}N_2S \cdot HCl$ requires: C, 58.53; H, 5.67; N, 10.50%. |
| 33 | $R_5$ = $R_6$ = F | 1 (i) | 21% | (Free-base purified by column chromatography, [$SiO_2$; ethyl acetate - methanol - ammonium hydroxide (92:7:1)]. Hydrochloride. m.p. 249–250° C.; NMR (400 MHz, DMSO-$d_6$) $\delta_H$ 1.18(3H, d, J 6.53 Hz), 2.45(2H, m), 2.72(2H, m), 2.77–2.94(2H, m), 3.55(1H, br s), 4.13(1H, dd, J 8.03 Hz, 15.06 Hz), 4.35(1H, dd, J 6.53 Hz, 14.56 Hz), 7.33(1H, dd, 8.03 Hz, 11.04 Hz), 7.72 (1H, dd, J 7.03 Hz, 12.05 Hz), 8.35(3H, br s). |
| 34 | $R_7$ = Cl<br>$R_6$ = Me | 1 (S) | 62% (i) | Hydrochloride. m.p. 250+° C. (dec.); NMR (400 MHz, DMSO-$d_6$) $\delta_H$ 8.14(3H, m, —$NH_3$), 7.36 (1H, d, J 8.5 Hz), 7.02(1H, d, J 8.5 Hz), 4.30(1H, dd, J 6.5, 15 Hz), 4.14(1H, dd, J 7.5, 14.5 Hz), 3.57(1H, m), 2.98(2H, app. t, J 7 Hz), 2.92–2.80 (2H, m), 2.48(2H, quint., J 7 Hz), 2.38(3H, s), 1.17(3H, d, J 6.5 Hz). |
| 35 | $R_7$ = Cl<br>$R_6$ = Me | 1 (R) | 44% (i) | Hydrochloride. m.p. 250+° C. (dec.); NMR (400 MHz, DMSO-$d_6$) $\delta_H$ 8.28(3H, m, —$NH_3$), 7.36 (1H, d, J 8.5 Hz), 7.01(1H, d, J 8.5 Hz), 4.34(1H, dd, J 6.5, 14.5 Hz), 4.15(1H, dd, J 1.5, 14.5 Hz), 3.56(1H, m), 2.98(1H, app. t, J 7 Hz), 2.93–2.80 (2H, m), 2.48(2H, quint., J 7 Hz), 2.38(3H, s), 1.17(3H, d, J 6.5 Hz). |
| 36 | $R_6$ = F<br>$R_5$ = OMe | 1 (R) | 75% (ii) | Fumarate. NMR (400 MHz, DMSO-$d_6$) $\delta_H$ 7.30 (1H, d, J 7.4 Hz), 7.14(1h, d, J 12.1 Hz), 6.51 (2H, s), 4.26(1H, dd, J 14.6, 5.8 Hz), 4.07(1H, dd, J 14.6, 7.0 Hz), 3.88(3H, s, MeO), 3.52(1H, br s), 2.91–2.78(2H, m), 2.74–2.68(2H, m), 2.45 (2H, obs quint, J 7.1 Hz), 1.11(3H, d, J 6.3 Hz); HPLC: [Xterra; 2.0 ml/min, methanol-10 mM aqueous ammonium acetate solution, gradient elution (50:50) to (80:20) over the first 4 min, then (80:20)] 97% (2.40 min). |
| 37 | $R_6$ = F<br>$R_5$ = OMe | 1 (S) | 100% (ii) | Fumarate. m.p. 213° C. (dec.); Found: C, 59.99; H, 6.24; N, 7.08%. $C_{19}H_{23}N_2O_5F$ requires: C, 60.31; H, 6.13; N, 7.40%. |
| 39 | $R_5$ = Cl<br>$R_6$ = F | 1 (R) | 58% (i) | Fumarate. NMR (400 MHz, DMSO-$d_6$) $\delta_H$ 7.75 (1H, d, J 6.5 Hz), 7.32(1H, d, J 10 Hz), 6.51(2H, s), 4.20(1H, dd, J 6.5, 14.5 Hz), 4.07(1H, dd, J 1, 14.5 Hz), 3.46(1H, m), 2.96–2.80(2H, m), 2.75 (2H, app. t, J 7 Hz), 2.47(2H, quint., J 7 Hz), 1.11 (3H, d, J 6.5 Hz); HPLC:[Xterra; 2.0 ml/min, |

-continued

| Example | Substitution pattern | n | Yield (method) | Data |
|---|---|---|---|---|
| 40 | $R_7$ = Cl<br>$R_6$ = F | 1<br>(R) | 98%<br>(i) | methanol-10 mM aqueous ammonium acetate solution, gradient elution (50:50) to (80:20) over the first 4 min, then (80:20)] 96% (4.72 min). Hydrochloride. m.p. 261–264° C. (ethyl acetate); Found: C, 53.92; H, 5.61; N, 8.97%. $C_{14}C_{16}ClFN_2 \cdot HCl \cdot 0.5H_2O$ requires: C, 53.86; H, 5.49; N, 8.97%. |
| 41 | $R_7$ = Br | 1<br>(S) | 97%<br>(i) | Hydrochloride. m.p. 246–252° C. (ethyl acetate); Found: C, 49.55; H, 5.45; N, 8.17%. $C_{14}H_{17}BrN_2 \cdot HCl \cdot 0.5H_2O$ requires: C, 49.65; H, 5.36; N, 8.27%. |
| 42 | $R_6$ = F<br>$R_7$ = OMe | 1<br>(S) | 37%<br>(ii) | Hemifumarate. NMR (400 MHz, DMSO-$d_6$) $\delta_H$ 7.14(1H, dd, J 8.8, 3.4 Hz), 6.90(1H, dd, J 11.7, 8.8 Hz), 6.47(1H, s), 4.07(1H, dd, J 14.5, 5.8 Hz), 3.99–3.94(1H, m), 3.90(3H, s, MeO), 3.35 (1H, br s), 2.90–2.79(4H, m), 2.47(2H, obs quint, J 7.1 Hz), 1.04(3H, d, J 5.4 Hz); HPLC: [Xterra; 2.0 ml/min, methanol-10 mM aqueous ammonium acetate solution, gradient elution (50:50) to (80:20) over the first 4 min, then 80:20] 99.4% (1.61 min). |
| 43 | $R_4$ = Cl | 1<br>(R) | 37%<br>(i) | m.p. 299–302° C. (2-propanol); Found: C, 58.79; H, 6.52; N, 9.48, Cl, 24.51%. $C_{14}H_{18}N_2Cl_2$ requires: C, 58.96; H, 6.36; N, 9.82; Cl, 24.86%. |
| 44 | $R_4$ = Cl | 1<br>(S) | 33%<br>(i) | m.p. 296–299° C. (2-propanol); NMR (400 MHz, DMSO-$d_6$) $\delta_H$ 8.45(3H, m, NH$_3$), 7.32(1H, dd, J 1, 8 Hz), 7.07(1H, dd, J 1.8 Hz), 6.99(1H, t, J 8 Hz), 4.62(1H, dd, J 6.5, 14.5 Hz), 4.47(1H, dd, J 6.5, 14.5 Hz), 3.62(1H, m), 3.32(1H, m), 3.00–2.80(2H, m), 2.76(2H, m), 2.50–2.43(2H, m), 1.13(3H, d, J 7 Hz). |
| 45 | 1-ketone | 1<br>(S) | 72%<br>(iii) | NMR (400 MHz, DMSO-$d_6$) $\delta_H$ 1.29(3H, d, J 6.53 Hz), 2.85(2H, m), 3.05–3.13(1H, m), 3.18–3.27(1H, m), 3.71(1H, m), 4.38(1H, dd, J 6.53 Hz, 14.56 Hz), 4.55(1H, dd, J 7.03 Hz, 15.06 Hz), 7.25(1H, m), 7.32(1H, dt, J 1.0 Hz, 7.03 Hz), 7.72, 1H, d, J 7.53 Hz), 7.77(1H, d, J 8.03 Hz), 8.58(3H, br s); HPLC: [Xterra; 2.0 ml/min, methanol-10 mM aqueous ammonium acetate solution (50:50)] 98% (2.11 min). |

What is claimed is:

1. A chemical compound of formula (I):

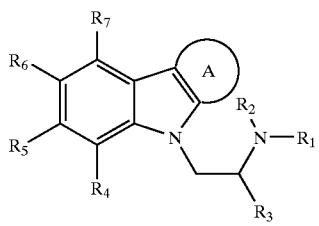

(I)

wherein:
$R_1$ and $R_2$ are independently selected from hydrogen and alkyl;
$R_3$ is alkyl;
$R_4$, $R_6$ and $R_7$ are independently selected from hydrogen, halogen, hydroxy, alkyl, aryl, amino, alkylamino, dialkylamino, alkoxy, aryloxy, alkylthio, alkylsulfoxyl, alkylsulfonyl, nitro, carbonitrile, carbo-alkoxy, carbo-aryloxy and carboxyl;
$R_5$ is selected from hydrogen, halogen, hydroxy, alkyl, aryl, amino, alkylamino, dialkylamino, alkoxy, aryloxy, alkylthio, alkylsulfoxyl, alkylsulfonyl, nitro, carbonitrile, carbo-alkoxy, carbo-aryloxy and carboxyl; and A is a 5-membered partially unsaturated or aromatic heterocyclic ring or a 5-membered partially unsaturated carbocyclic ring,
or a pharmaceutically acceptable salt, addition compound or prodrug thereof.

2. A compound according to claim 1 wherein $R_1$ and $R_2$ am selected from hydrogen and lower alkyl.

3. A compound according to claim 1 wherein $R_1$ and $R_2$ are hydrogen.

4. A compound according to claim 1, wherein $R_3$ is lower alkyl.

5. A compound according to claim 1, wherein $R_3$ is methyl.

6. A compound according to claim 1, wherein $R_4$ is selected from hydrogen, halogen, alkyl and alkoxy.

7. A compound according to claim 1, wherein $R_4$ is hydrogen.

8. A compound according to claim 1, wherein $R_6$ is selected from hydrogen and halogen.

9. A compound according to claim 1, wherein $R_7$ is selected from hydrogen, halogen and alkoxy.

10. A compound according to claim 1, wherein A is partially unsaturated.

11. A compound according to claim 1, wherein A contains a heteroatom selected from N, O and S.

12. A compound according to claim 1, wherein A is a 5-membered partially unsaturated carbocyclic ring or a 5-membered partially unsaturated or aromatic heterocyclic ring.

13. A compound according to claim 1, wherein A is selected from cyclopentenyl and thienyl.

14. A compound according to claim 1 which is selected from the group consisting of (S)-1-(7,8-difluoro-1,2,3,4-tetrahydrocyclopent[b]indol-4-yl)-2-propylamine, (S)-1-(7-fluoro-1,2,3,4-tetrahydrocyclopent[b]indol4-yl)-2-propylamine, (S)-1-(8-chloro-1,2,3,4-tetrahydrocyclopent[b]indol-4-yl)-2-propylamine, (S)-1-(6-methoxy-1,2,3,4-tetrahydrocyclopent[b]indol-4-yl)-2-propylamine, (S)-1-(7-fluoro-6-methoxy-1,2,3,4-tetrahydrocyclopent[b]indol-4-yl)-2-propylamine, (S)-1-(7-fluoro-8-methoxy-1,2,3,4-tetrahydrocyclopent[b]indol-4-yl)-2-propylamine, (S)-1-(8-chloro-7-fluoro-1,2,3,4-tetrahydrocyclopent[b]indol-4-yl)-2-propylamine, (S)-1-(1,2,3,4-tetrahydrocyclopent[b]indol-4-yl)-2-propylamine and (R)-1-(1,2,3,4-tetrahydrocyclopent[b]indol-4-yl)-2-propylamine.

15. A method of treatment of disorders of the central nervous system; damage to the central nervous system; cardiovascular disorders; gastrointestinal disorders; diabetes insipidus, and sleep apnea, comprising administering to a patient in need of such treatment an effective dose of a compound of formula (I) as set out in claim 1.

16. A method of treatment according to claim 15 wherein said disorder is obesity.

17. A method according to claim 15 wherein said treatment is prophylactic treatment.

18. A pharmaceutical composition comprising a compound of formula (I) as set out in claim 1, in combination with a pharmaceutically acceptable carrier or excipient.

19. A method according to claim 15 wherein the disorders of the central nervous system are selected from the group consisting of depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioral disorders, behavioral disorders associated with dementia, organic mental disorders, mental disorders in childhood, aggressivity, age-related memory disorders, chronic fatigue syndrome, drug and alcohol addiction, obesity, bulimia, anorexia nervosa and premenstrual tension.

20. A method according to claim 15 wherein the damage to the central nervous system is by trauma, stroke, neurodegenerative disease or toxic or infective CNS diseases.

21. A method according to claim 20 wherein said toxic or infective CNS disease is encephalitis or meningitis.

22. A method according to claim 15 wherein the cardiovascular disorder is thrombosis.

23. A method according to claim 15 wherein the gastrointestinal disorder is dysfunction of gastrointestinal motility.

* * * * *